US012733950B2

(12) United States Patent
Kingsley et al.

(10) Patent No.: US 12,733,950 B2
(45) Date of Patent: Sep. 15, 2026

(54) END EFFECTOR ASSEMBLY, INSTRUMENT, SYSTEM, AND METHOD FACILITATING TESTING AND/OR CALIBRATION OF A SURGICAL INSTRUMENT

(71) Applicant: Covidien LP, Mansfield, MA (US)

(72) Inventors: Dylan R. Kingsley, Broomfield, CO (US); Christopher T. Tschudy, Arvada, CO (US); Jason G. Weihe, Longmont, CO (US); Zachary S. Heiliger, Nederland, CO (US); William R. Whitney, Boulder, CO (US); Curtis M. Siebenaller, Frederick, CO (US); Haralambos P. Apostolopoulos, Westminster, CO (US); Russell W. Holbrook, Naples, FL (US); Matthew D. Straka, Arvada, CO (US); Reid Thomson, Loveland, CO (US); Carolyn Girvin, Boulder, CO (US); Jared N. Farlow, Los Angeles, CA (US); Colin H. Murphy, Cambridge, MA (US); Zachary T. Morgan, Boston, MA (US); Gary J. Suszynski, Woodbury, CT (US); Aaron J. Clippinger, Deep River, CT (US)

(73) Assignee: Covidien LP, Mansfield, MA (US)

( * ) Notice: Subject to any disclaimer, the term of this patent is extended or adjusted under 35 U.S.C. 154(b) by 791 days.

(21) Appl. No.: 18/074,993

(22) Filed: Dec. 5, 2022

(65) Prior Publication Data

US 2023/0181207 A1 Jun. 15, 2023

Related U.S. Application Data

(60) Provisional application No. 63/309,697, filed on Feb. 14, 2022, provisional application No. 63/288,716, filed on Dec. 13, 2021.

(51) Int. Cl.
*A61B 17/285* (2006.01)
*A61B 17/00* (2006.01)
*A61B 34/30* (2016.01)

(52) U.S. Cl.
CPC ............ *A61B 17/285* (2013.01); *A61B 34/30* (2016.02); *A61B 2017/00681* (2013.01)

(58) Field of Classification Search
CPC .................. A61B 17/28; A61B 17/282; A61B 2017/2926; A61B 2018/0225
See application file for complete search history.

(56) References Cited

U.S. PATENT DOCUMENTS 5,860,995 A * 1/1999 Berkelaar .............. A61B 17/29 606/174
6,132,368 A 10/2000 Cooper
(Continued)

FOREIGN PATENT DOCUMENTS

| | | | |
|---|---|---|---|
| CN | 113280956 | A | 8/2021 |
| NO | 2018013217 | A1 | 1/2018 |
| WO | 2008134471 | A1 | 11/2008 |

OTHER PUBLICATIONS

Partial European Search Report issued in corresponding European Application No. 22213047.8 dated Apr. 17, 2023, 15 pages.
(Continued)

*Primary Examiner* — Martin T Ton

(57) ABSTRACT

An end effector assembly of a surgical instrument includes a clevis defining a longitudinal axis and including first and second arms spaced-apart relative to one another and first and second jaw members supported by the clevis. At least one of the jaw members is movable relative to the other and the clevis between a spaced-apart position and an approximated position for grasping tissue between the jaw members. The clevis includes first and second locating features on outwardly-facings sides of the first and second spaced-
(Continued)

apart arms, respectively. The first and second locating features are configured to facilitate engagement and alignment of the end effector assembly within a test fixture.

16 Claims, 17 Drawing Sheets

(56) References Cited

U.S. PATENT DOCUMENTS 6,206,903 B1 3/2001 Ramans
6,246,200 B1 6/2001 Blumenkranz et al.
6,312,435 B1 11/2001 Wallace et al.
6,331,181 B1 12/2001 Tierney et al.
6,358,268 B1 * 3/2002 Hunt .................... A61B 17/29 606/206
6,394,998 B1 5/2002 Wallace et al.
6,424,885 B1 7/2002 Niemeyer et al.
6,441,577 B2 8/2002 Blumenkranz et al.
6,459,926 B1 10/2002 Nowlin et al.
6,491,691 B1 12/2002 Morley et al.
6,491,701 B2 12/2002 Tierney et al.
6,493,608 B1 12/2002 Niemeyer
6,565,554 B1 5/2003 Niemeyer
6,645,196 B1 11/2003 Nixon et al.
6,659,939 B2 12/2003 Moll
6,671,581 B2 12/2003 Niemeyer et al.
6,676,684 B1 1/2004 Morley et al.
6,685,698 B2 2/2004 Morley et al.
6,699,235 B2 3/2004 Wallace et al.
6,714,839 B2 3/2004 Salisbury, Jr. et al.
6,716,233 B1 4/2004 Whitman
6,728,599 B2 4/2004 Wang et al.
6,746,443 B1 6/2004 Morley et al.
6,766,204 B2 7/2004 Niemeyer et al.
6,770,081 B1 8/2004 Cooper et al.
6,772,053 B2 8/2004 Niemeyer
6,783,524 B2 8/2004 Anderson et al.
6,793,652 B1 9/2004 Whitman et al.
6,793,653 B2 9/2004 Sanchez et al.
6,799,065 B1 9/2004 Niemeyer
6,837,883 B2 1/2005 Moll et al.
6,839,612 B2 1/2005 Sanchez et al.
6,840,938 B1 1/2005 Morley et al.
6,843,403 B2 1/2005 Whitman
6,846,309 B2 1/2005 Whitman et al.
6,866,671 B2 3/2005 Tierney et al.
6,871,117 B2 3/2005 Wang et al.
6,879,880 B2 4/2005 Nowlin et al.
6,899,705 B2 5/2005 Niemeyer
6,902,560 B1 6/2005 Morley et al.
6,936,042 B2 8/2005 Wallace et al.
6,951,535 B2 10/2005 Ghodoussi et al.
6,974,449 B2 12/2005 Niemeyer
6,991,627 B2 1/2006 Madhani et al.
6,994,708 B2 2/2006 Manzo
7,048,745 B2 5/2006 Tierney et al.
7,066,926 B2 6/2006 Wallace et al.
7,118,582 B1 10/2006 Wang et al.
7,125,403 B2 10/2006 Julian et al.
7,155,315 B2 12/2006 Niemeyer et al.
7,239,940 B2 7/2007 Wang et al.
7,306,597 B2 12/2007 Manzo
7,357,774 B2 4/2008 Cooper
7,373,219 B2 5/2008 Nowlin et al.
7,379,790 B2 5/2008 Toth et al.
7,386,365 B2 6/2008 Nixon
7,391,173 B2 6/2008 Schena
7,398,707 B2 7/2008 Morley et al.
7,413,565 B2 8/2008 Wang et al.
7,453,227 B2 11/2008 Prisco et al.
7,524,320 B2 4/2009 Tierney et al.
7,574,250 B2 8/2009 Niemeyer
7,594,912 B2 9/2009 Cooper et al.
7,607,440 B2 10/2009 Coste-Maniere et al.
7,666,191 B2 2/2010 Orban, III et al.
7,682,357 B2 3/2010 Ghodoussi et al.
7,689,320 B2 3/2010 Prisco et al.
7,695,481 B2 4/2010 Wang et al.
7,695,485 B2 4/2010 Whitman et al.
7,699,855 B2 4/2010 Anderson et al.
7,713,263 B2 5/2010 Niemeyer
7,725,214 B2 5/2010 Diolaiti
7,727,244 B2 6/2010 Orban, III et al.
7,741,802 B2 6/2010 Prisco
7,756,036 B2 7/2010 Druke et al.
7,757,028 B2 7/2010 Druke et al.
7,762,825 B2 7/2010 Burbank et al.
7,778,733 B2 8/2010 Nowlin et al.
7,803,151 B2 9/2010 Whitman
7,806,891 B2 10/2010 Nowlin et al.
7,819,859 B2 10/2010 Prisco et al.
7,819,885 B2 10/2010 Cooper
7,824,401 B2 11/2010 Manzo et al.
7,835,823 B2 11/2010 Sillman et al.
7,843,158 B2 11/2010 Prisco
7,865,266 B2 1/2011 Moll et al.
7,865,269 B2 1/2011 Prisco et al.
7,886,743 B2 2/2011 Cooper et al.
7,899,578 B2 3/2011 Prisco et al.
7,907,166 B2 3/2011 Lamprecht et al.
7,935,130 B2 5/2011 Williams
7,963,913 B2 6/2011 Devengenzo et al.
7,983,793 B2 7/2011 Toth et al.
8,002,767 B2 8/2011 Sanchez
8,004,229 B2 8/2011 Nowlin et al.
8,012,170 B2 9/2011 Whitman et al.
8,054,752 B2 11/2011 Druke et al.
8,062,288 B2 11/2011 Cooper et al.
8,079,950 B2 12/2011 Stern et al.
8,100,133 B2 1/2012 Mintz et al.
8,108,072 B2 1/2012 Zhao et al.
8,120,301 B2 2/2012 Goldberg et al.
8,142,447 B2 3/2012 Cooper et al.
8,147,503 B2 4/2012 Zhao et al.
8,151,661 B2 4/2012 Schena et al.
8,155,479 B2 4/2012 Hoffman et al.
8,182,469 B2 5/2012 Anderson et al.
8,202,278 B2 6/2012 Orban, III et al.
8,206,406 B2 6/2012 Orban, III
8,210,413 B2 7/2012 Whitman et al.
8,216,250 B2 7/2012 Orban, III et al.
8,220,468 B2 7/2012 Cooper et al.
8,256,319 B2 9/2012 Cooper et al.
8,285,517 B2 10/2012 Sillman et al.
8,315,720 B2 11/2012 Mohr et al.
8,335,590 B2 12/2012 Costa et al.
8,347,757 B2 1/2013 Duval
8,374,723 B2 2/2013 Zhao et al.
8,418,073 B2 4/2013 Mohr et al.
8,419,717 B2 4/2013 Diolaiti et al.
8,423,182 B2 4/2013 Robinson et al.
8,452,447 B2 5/2013 Nixon
8,454,585 B2 6/2013 Whitman
8,499,992 B2 8/2013 Whitman et al.
8,508,173 B2 8/2013 Goldberg et al.
8,528,440 B2 9/2013 Morley et al.
8,529,582 B2 9/2013 Devengenzo et al.
8,540,748 B2 9/2013 Murphy et al.
8,551,116 B2 10/2013 Julian et al.
8,562,594 B2 10/2013 Cooper et al.
8,594,841 B2 11/2013 Zhao et al.
8,597,182 B2 12/2013 Stein et al.
8,597,280 B2 12/2013 Cooper et al.
8,600,551 B2 12/2013 Itkowitz et al.
8,608,773 B2 12/2013 Tierney et al.
8,620,473 B2 12/2013 Diolaiti et al.
8,624,537 B2 1/2014 Nowlin et al.
8,634,957 B2 1/2014 Toth et al.
8,638,056 B2 1/2014 Goldberg et al.
8,638,057 B2 1/2014 Goldberg et al.
8,644,988 B2 2/2014 Prisco et al.
8,666,544 B2 3/2014 Moll et al.
8,668,638 B2 3/2014 Donhowe et al.

(56) References Cited

U.S. PATENT DOCUMENTS 8,746,252 B2 6/2014 McGrogan et al.
8,749,189 B2 6/2014 Nowlin et al.
8,749,190 B2 6/2014 Nowlin et al.
8,758,352 B2 6/2014 Cooper et al.
8,761,930 B2 6/2014 Nixon
8,768,516 B2 7/2014 Diolaiti et al.
8,786,241 B2 7/2014 Nowlin et al.
8,790,243 B2 7/2014 Cooper et al.
8,808,164 B2 8/2014 Hoffman et al.
8,816,628 B2 8/2014 Nowlin et al.
8,821,480 B2 9/2014 Burbank
8,823,308 B2 9/2014 Nowlin et al.
8,827,989 B2 9/2014 Niemeyer
8,838,270 B2 9/2014 Druke et al.
8,852,174 B2 10/2014 Burbank
8,858,547 B2 10/2014 Brogna
8,862,268 B2 10/2014 Robinson et al.
8,864,751 B2 10/2014 Prisco et al.
8,864,752 B2 10/2014 Diolaiti et al.
8,903,546 B2 12/2014 Diolaiti et al.
8,903,549 B2 12/2014 Itkowitz et al.
8,911,428 B2 12/2014 Cooper et al.
8,912,746 B2 12/2014 Reid et al.
8,944,070 B2 2/2015 Guthart
8,989,903 B2 3/2015 Weir et al.
9,002,518 B2 4/2015 Manzo
9,014,856 B2 4/2015 Manzo et al.
9,016,540 B2 4/2015 Whitman et al.
9,019,345 B2 4/2015 O'Grady et al.
9,043,027 B2 5/2015 Durant et al.
9,050,120 B2 6/2015 Swarup et al.
9,055,961 B2 6/2015 Manzo et al.
9,068,628 B2 6/2015 Solomon et al.
9,078,684 B2 7/2015 Williams
9,084,623 B2 7/2015 Gomez et al.
9,095,362 B2 8/2015 Dachs, II et al.
9,096,033 B2 8/2015 Holop et al.
9,101,381 B2 8/2015 Burbank et al.
9,113,877 B1 8/2015 Whitman et al.
9,138,284 B2 9/2015 Krom et al.
9,144,456 B2 9/2015 Rosa et al.
9,198,730 B2 12/2015 Prisco et al.
9,204,923 B2 12/2015 Manzo et al.
9,226,648 B2 1/2016 Saadat et al.
9,226,750 B2 1/2016 Weir et al.
9,226,761 B2 1/2016 Burbank
9,232,984 B2 1/2016 Guthart et al.
9,241,766 B2 1/2016 Duque et al.
9,241,767 B2 1/2016 Prisco et al.
9,241,769 B2 1/2016 Arkin et al.
9,259,275 B2 2/2016 Burbank
9,259,277 B2 2/2016 Rogers et al.
9,259,281 B2 2/2016 Griffiths et al.
9,259,282 B2 2/2016 Azizian et al.
9,261,172 B2 2/2016 Solomon et al.
9,265,567 B2 2/2016 Orban, III et al.
9,265,584 B2 2/2016 Itkowitz et al.
9,283,049 B2 3/2016 Diolaiti et al.
9,301,811 B2 4/2016 Goldberg et al.
9,314,307 B2 4/2016 Richmond et al.
9,317,651 B2 4/2016 Nixon
9,345,546 B2 5/2016 Toth et al.
9,393,017 B2 7/2016 Flanagan et al.
9,402,689 B2 8/2016 Prisco et al.
9,417,621 B2 8/2016 Diolaiti
9,424,303 B2 8/2016 Hoffman et al.
9,433,418 B2 9/2016 Whitman et al.
9,446,517 B2 9/2016 Burns et al.
9,452,020 B2 9/2016 Griffiths et al.
9,474,569 B2 10/2016 Manzo et al.
9,480,533 B2 11/2016 Devengenzo et al.
9,503,713 B2 11/2016 Zhao et al.
9,550,300 B2 1/2017 Danitz et al.
9,554,859 B2 1/2017 Nowlin et al.
9,566,124 B2 2/2017 Prisco et al.
9,579,164 B2 2/2017 Itkowitz et al.
9,585,641 B2 3/2017 Cooper et al.
9,615,883 B2 4/2017 Schena et al.
9,623,563 B2 4/2017 Nixon
9,623,902 B2 4/2017 Griffiths et al.
9,629,520 B2 4/2017 Diolaiti
9,662,177 B2 5/2017 Weir et al.
9,664,262 B2 5/2017 Donlon et al.
9,675,354 B2 6/2017 Weir et al.
9,687,312 B2 6/2017 Dachs, II et al.
9,700,334 B2 7/2017 Hinman et al.
9,718,190 B2 8/2017 Larkin et al.
9,730,719 B2 8/2017 Brisson et al.
9,737,199 B2 8/2017 Pistor et al.
9,795,446 B2 10/2017 DiMaio et al.
9,797,484 B2 10/2017 Solomon et al.
9,801,690 B2 10/2017 Larkin et al.
9,814,530 B2 11/2017 Weir et al.
9,814,536 B2 11/2017 Goldberg et al.
9,814,537 B2 11/2017 Itkowitz et al.
9,820,823 B2 11/2017 Richmond et al.
9,827,059 B2 11/2017 Robinson et al.
9,830,371 B2 11/2017 Hoffman et al.
9,839,481 B2 12/2017 Blumenkranz et al.
9,839,487 B2 12/2017 Dachs, II
9,850,994 B2 12/2017 Schena
9,855,102 B2 1/2018 Blumenkranz
9,855,107 B2 1/2018 Labonville et al.
9,872,737 B2 1/2018 Nixon
9,877,718 B2 1/2018 Weir et al.
9,883,920 B2 2/2018 Blumenkranz
9,888,974 B2 2/2018 Niemeyer
9,895,813 B2 2/2018 Blumenkranz et al.
9,901,408 B2 2/2018 Larkin
9,918,800 B2 3/2018 Itkowitz et al.
9,943,375 B2 4/2018 Blumenkranz et al.
9,948,852 B2 4/2018 Lilagan et al.
9,949,798 B2 4/2018 Weir
9,949,802 B2 4/2018 Cooper
9,952,107 B2 4/2018 Blumenkranz et al.
9,956,044 B2 5/2018 Gomez et al.
9,980,778 B2 5/2018 Ohline et al.
10,008,017 B2 6/2018 Itkowitz et al.
10,028,793 B2 7/2018 Griffiths et al.
10,033,308 B2 7/2018 Chaghajerdi et al.
10,034,719 B2 7/2018 Richmond et al.
10,052,167 B2 8/2018 Au et al.
10,085,811 B2 10/2018 Weir et al.
10,092,344 B2 10/2018 Mohr et al.
10,123,844 B2 11/2018 Nowlin
10,130,366 B2 11/2018 Shelton, IV et al.
10,188,471 B2 1/2019 Brisson
10,201,390 B2 2/2019 Swarup et al.
10,213,202 B2 2/2019 Flanagan et al.
10,258,416 B2 4/2019 Mintz et al.
10,278,782 B2 5/2019 Jarc et al.
10,278,783 B2 5/2019 Itkowitz et al.
10,282,881 B2 5/2019 Itkowitz et al.
10,335,242 B2 7/2019 Devengenzo et al.
10,405,934 B2 9/2019 Prisco et al.
10,433,922 B2 10/2019 Itkowitz et al.
10,464,219 B2 11/2019 Robinson et al.
10,485,621 B2 11/2019 Morrissette et al.
10,500,004 B2 12/2019 Hanuschik et al.
10,500,005 B2 12/2019 Weir et al.
10,500,007 B2 12/2019 Richmond et al.
10,507,066 B2 12/2019 DiMaio et al.
10,510,267 B2 12/2019 Jarc et al.
10,524,871 B2 1/2020 Liao
10,548,459 B2 2/2020 Itkowitz et al.
10,575,909 B2 3/2020 Robinson et al.
10,592,529 B2 3/2020 Hoffman et al.
10,595,946 B2 3/2020 Nixon
10,881,469 B2 1/2021 Robinson
10,881,473 B2 1/2021 Itkowitz et al.
10,898,188 B2 1/2021 Burbank
10,898,189 B2 1/2021 McDonald, II
10,905,506 B2 2/2021 Itkowitz et al.
10,912,544 B2 2/2021 Brisson et al.

(56) References Cited

U.S. PATENT DOCUMENTS 10,912,619 B2 2/2021 Jarc et al.
10,918,387 B2 2/2021 Duque et al.
10,918,449 B2 2/2021 Solomon et al.
10,932,873 B2 3/2021 Griffiths et al.
10,932,877 B2 3/2021 Devengenzo et al.
10,939,969 B2 3/2021 Swarup et al.
10,939,973 B2 3/2021 DiMaio et al.
10,952,801 B2 3/2021 Miller et al.
10,965,933 B2 3/2021 Jarc
10,966,742 B2 4/2021 Rosa et al.
10,973,517 B2 4/2021 Wixey
10,973,519 B2 4/2021 Weir et al.
10,984,567 B2 4/2021 Itkowitz et al.
10,993,773 B2 5/2021 Cooper et al.
10,993,775 B2 5/2021 Cooper et al.
11,000,331 B2 5/2021 Krom et al.
11,013,567 B2 5/2021 Wu et al.
11,020,138 B2 6/2021 Ragosta
11,020,191 B2 6/2021 Diolaiti et al.
11,020,193 B2 6/2021 Wixey et al.
11,026,755 B2 6/2021 Weir et al.
11,026,759 B2 6/2021 Donlon et al.
11,040,189 B2 6/2021 Vaders et al.
11,045,077 B2 6/2021 Stern et al.
11,045,274 B2 6/2021 Dachs, II et al.
11,058,501 B2 7/2021 Tokarchuk et al.
11,076,925 B2 8/2021 DiMaio et al.
11,090,119 B2 8/2021 Burbank
11,096,687 B2 8/2021 Flanagan et al.
11,098,803 B2 8/2021 Duque et al.
11,109,925 B2 9/2021 Cooper et al.
11,116,578 B2 9/2021 Hoffman et al.
11,129,683 B2 9/2021 Steger et al.
11,135,029 B2 10/2021 Suresh et al.
11,147,552 B2 10/2021 Burbank et al.
11,147,640 B2 10/2021 Jarc et al.
11,154,373 B2 10/2021 Abbott et al.
11,154,374 B2 10/2021 Hanuschik et al.
11,160,622 B2 11/2021 Goldberg et al.
11,160,625 B2 11/2021 Wixey et al.
11,161,243 B2 11/2021 Rabindran et al.
11,166,758 B2 11/2021 Mohr et al.
11,166,770 B2 11/2021 DiMaio et al.
11,166,773 B2 11/2021 Ragosta et al.
11,173,597 B2 11/2021 Rabindran et al.
11,185,378 B2 11/2021 Weir et al.
11,191,596 B2 12/2021 Thompson et al.
11,197,729 B2 12/2021 Thompson et al.
11,213,360 B2 1/2022 Hourtash et al.
11,221,863 B2 1/2022 Azizian et al.
11,234,700 B2 2/2022 Ragosta et al.
11,241,274 B2 2/2022 Vaders et al.
11,241,290 B2 2/2022 Waterbury et al.
11,259,870 B2 3/2022 DiMaio et al.
11,259,884 B2 3/2022 Burbank
11,272,993 B2 3/2022 Gomez et al.
11,272,994 B2 3/2022 Saraliev et al.
11,291,442 B2 4/2022 Wixey et al.
11,291,513 B2 4/2022 Manzo et al.
2001/0056283 A1* 12/2001 Carter .............. A61B 17/06066 606/148
2011/0036183 A1* 2/2011 Artale .................... A61B 90/06 73/862.621
2011/0163147 A1* 7/2011 Laurent ................ A61B 17/072 227/175.1
2019/0298466 A1* 10/2019 Klein ..................... A61B 34/70
2021/0106353 A1* 4/2021 Lester .................. A61B 17/282
2022/0117623 A1* 4/2022 Craig ............. A61B 17/320092
2022/0117679 A1* 4/2022 Tschudy ................. A61B 34/00

OTHER PUBLICATIONS

Extended European Search Report for Application No. 22213047.8 dated Jul. 20, 2023, 13 pages.

* cited by examiner

END EFFECTOR ASSEMBLY, INSTRUMENT, SYSTEM, AND METHOD FACILITATING TESTING AND/OR CALIBRATION OF A SURGICAL INSTRUMENT

CROSS-REFERENCE TO RELATED APPLICATION

This application claims the benefit of, and priority to, U.S. Provisional Patent Application No. 63/288,716, filed on Dec. 13, 2021, and U.S. Provisional Patent Application No. 63/309,697, filed on Feb. 14, 2022, the entire contents of each of which are hereby incorporated herein by reference.

FIELD

This disclosure relates to surgical instrument testing and/or calibration and, more specifically, to an end effector assembly, instrument, system, and method facilitating testing and/or calibration of a surgical instrument such as, for example, for use in surgical robotic systems.

BACKGROUND

Surgical robotic systems are increasingly utilized in various different surgical procedures. Some surgical robotic systems include a console supporting a robotic arm. One or more different surgical instruments may be configured for use with the surgical robotic system and selectively mountable to the robotic arm. The robotic arm provides one or more inputs to the mounted surgical instrument to enable remote operation of the mounted surgical instrument.

A surgical forceps, one type of instrument capable of being utilized with a robotic surgical system, relies on mechanical action between its jaw members to grasp, clamp, and constrict tissue. Electrosurgical forceps utilize both controlled mechanical clamping action and energy to heat tissue to treat, e.g., coagulate, cauterize, or seal, tissue. Typically, once tissue is treated, the tissue is severed using a cutting element. Accordingly, electrosurgical forceps are designed to incorporate a cutting element to effectively sever treated tissue. Alternatively, energy based, e.g., thermal, electrical, ultrasonic, etc., cutting mechanisms may be implemented.

Due to the remote operation of surgical robotic instruments, whether electrosurgical forceps or other surgical robotic instruments, actuation of the instrument needs to exactly reflect the movement commands input remotely at a surgical console. Thus, prior to using the instruments, the robotic systems calibrate the instruments.

SUMMARY

As used herein, the term “distal” refers to the portion that is being described which is farther from an operator (whether a human surgeon or a surgical robot), while the term “proximal” refers to the portion that is being described which is closer to the operator. Terms including “generally,” “about,” “substantially,” and the like, as utilized herein, are meant to encompass variations, e.g., manufacturing tolerances, material tolerances, use and environmental tolerances, measurement variations, design variations, and/or other variations, up to and including plus or minus 10 percent. To the extent consistent, any of the aspects described herein may be used in conjunction with any or all of the other aspects described herein.

Provided in accordance with aspects of this disclosure is an end effector assembly of a surgical instrument including a clevis defining a longitudinal axis and including first and second arms spaced-apart relative to one another, and first and second jaw members supported by the clevis. At least one of the first or second jaw members is movable relative to the other of the first or second jaw members and the clevis between a spaced-apart position and an approximated position for grasping tissue between the first and second jaw members. The clevis includes first and second locating features on outwardly-facings sides of the first and second spaced-apart arms, respectively. The first and second locating features are configured to facilitate engagement and alignment of the end effector assembly within a test fixture.

In an aspect of this disclosure, the first and second locating features define an axis therethrough that is substantially perpendicular relative to the longitudinal axis of the clevis.

In another aspect of this disclosure, the first and second locating features are recesses defined within outwardly-facings surfaces of the outwardly-facings sides of the first and second spaced-apart arms, respectively.

In yet another aspect of this disclosure, the second jaw member is fixed relative to the clevis and the first jaw member is pivotable relative to the second jaw member and the clevis.

In still another aspect of this disclosure, the end effector assembly further includes a knife configured for deployment between the first and second jaw members.

A system provided in accordance with this disclosure includes a surgical instrument and a test fixture. The surgical instrument includes an articulating shaft and an end effector assembly disposed at a distal end of the articulating shaft. The end effector assembly includes a clevis defining a longitudinal axis and including first and second arms spaced-apart relative to one another, and first and second jaw members supported by the clevis. At least one of the first or second jaw members is movable relative to the other of the first or second jaw members and the clevis between a spaced-apart position and an approximated position for grasping tissue between the first and second jaw members. The clevis includes first and second locating features on outwardly-facings sides of the first and second spaced-apart arms, respectively. The test fixture includes a base including a clevis-receiving area and first and second supports on either side of the clevis-receiving area. The clevis-receiving area is configured to receive the clevis of the end effector assembly therein while the first and second supports include first and second retention features, respectively configured to engage the first and second locating features of the clevis, respectively, to thereby engage and align the end effector assembly relative to the test fixture. The test fixture further includes at least one sensor configured to obtain a measurement associated with an actuation of the end effector assembly.

In an aspect of this disclosure, the first and second locating features define an axis therethrough that is substantially perpendicular relative to the longitudinal axis of the clevis.

In another aspect of this disclosure, the first and second locating features are recesses defined within outwardly-facings surfaces of the outwardly-facings sides of the first and second spaced-apart arms, respectively, and the first and second retention features are pins extending inwardly from the first and second supports, respectively.

In still another aspect of this disclosure, the base of the test fixture further includes a jaw-receiving area configured to receive the first and second jaw members of the end effector assembly therein.

In yet another aspect of this disclosure, the at least one sensor includes at least one, at least two of, or each of: a jaw pressure or force sensor, a jaw spacing sensor, a knife detection sensor, or an articulation sensor. Other suitable sensors are also contemplated such as, for example, a thermal camera, thermal sensor, and/or any other suitable sensor configured to measure performance, position, alignment, temperature, force, etc.

In still yet another aspect of this disclosure, the test fixture includes at least one interchangeable module including the at least one sensor thereon.

In another aspect of this disclosure, the at least one of the first or second jaw members is movable between the spaced-apart position and the approximated position with the end effector assembly engaged within the test fixture. Additionally or alternatively, the end effector assembly is configured to articulate when engaged within the test fixture to articulate the test fixture therewith. Further, the end effector assembly may include a knife configured for deployment between the first and second jaw members with the end effector assembly engaged within the test fixture.

In another aspect of this disclosure, the system further includes a second test fixture similar to the test fixture except that the second test fixture includes at least one sensor different from the at least one sensor of the test fixture.

A method of testing an end effector assembly of surgical instrument in accordance with this disclosure includes securing a clevis of an end effector assembly to a test fixture such that at least one sensor of the test fixture is aligned with the end effector assembly. The securing includes engaging cooperating locating features and retention features associated with the clevis and the test fixture, respectively. The method further includes actuating the end effector assembly, obtaining measurement data associated with the actuation of the end effector assembly using the at least one sensor, and recording the measurement data.

In an aspect of this disclosure, the method further includes sequentially repeating the actuation and obtaining a plurality of times.

In another aspect of this disclosure, the actuating includes at least one of articulating the end effector assembly, moving at least one jaw member of the end effector assembly, or deploying a knife through the end effector assembly.

In another aspect of this disclosure, the recording includes storing the measurement data in a memory associated with a surgical instrument having the end effector assembly attached thereto.

A surgical robotic system provided in accordance with this disclosure includes a robotic arm and a calibration attachment. The robotic arm includes a port latch configured to hold an access port. The calibration attachment includes a base configured to couple to the access port and a tube including a first end portion coupled to the base and a second end portion. The tube defines a lumen configured for receipt of a surgical instrument and calibration of the surgical instrument therein.

In an aspect of this disclosure, the calibration attachment further includes a funnel disposed at the second end portion.

In another aspect of this disclosure, the calibration attachment further includes a clip coupled to the base and movable to secure the base to the access port.

In another aspect of this disclosure, the tube has an inner diameter smaller than an inner diameter of a canula portion of an access port coupled to the base.

In still another aspect of this disclosure, the system further includes a sliding mechanism coupled to the robotic arm, an instrument drive unit disposed on the sliding mechanism, and a surgical instrument configured to couple to the instrument drive unit. The surgical instrument includes an end effector assembly.

In yet another aspect of this disclosure, the system further includes a controller configured to control the sliding mechanism to move the instrument drive unit and the surgical instrument toward the calibration attachment.

In still yet another aspect of this disclosure, the controller is further configured to determine whether the end effector assembly is disposed within the tube. In such aspects, the controller may be further configured to calibrate the end effector assembly once the end effector assembly is disposed within the tube.

In another aspect of this disclosure, the end effector assembly includes at least one degree of freedom.

In yet another aspect of this disclosure, calibration of the end effector assembly includes moving the end effector assembly against opposing sides of the tube.

Also provided in accordance with aspects of this disclosure is calibration attachment including a base configured to couple to an access port and a tube including a first end portion coupled to the base. The tube further includes a second end portion and defines a lumen configured for receipt of a surgical instrument and calibration of the surgical instrument therein.

In an aspect of this disclosure, the calibration attachment further includes funnel disposed at the second end portion of the tube.

In another aspect of this disclosure, the calibration attachment further includes a clip coupled to the base and movable to secure the base to the access port.

In still another aspect of this disclosure, the tube has an inner diameter smaller than an inner diameter of a canula portion of an access port coupled to the base.

In yet another aspect of this disclosure, each of the base and the tube is formed from at least one of a metal or a polymer. Additionally or alternatively, the base has a circular, concave shape configured to engage an access port.

A method for calibrating a robotic surgical instrument in accordance with aspects of this disclosure includes moving an instrument drive unit coupled to a surgical instrument having an end effector assembly along a sliding mechanism disposed on a robotic arm, measuring insertion distance of the end effector assembly relative to a calibration attachment coupled to an access port, determining whether the end effector assembly reached a calibration position, and calibrating the end effector assembly within the calibration attachment.

In an aspect of this disclosure, the method further includes moving the surgical instrument until the end effector assembly is disposed within a tube of the calibration attachment.

In another aspect of this disclosure, calibrating the end effector assembly includes moving the end effector assembly against opposing sides of the tube.

In still yet another aspect of this disclosure, the method further includes securing the calibration attachment to the access port via a flexible clip.

BRIEF DESCRIPTION OF THE DRAWINGS

The above and other aspects and features of this disclosure will become more apparent in view of the following detailed description when taken in conjunction with the accompanying drawings wherein like reference numerals identify similar or identical elements.

DETAILED DESCRIPTION

This disclosure provides an end effector assembly of a surgical instrument, surgical instrument, system, and method facilitating testing and/or calibration of the surgical instrument. As described in detail below, the end effector assembly, instrument, system, and method of this disclosure are configured for use with a surgical robotic system, which may include, for example, a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which, in turn, move the robotic arm in response to the movement command. Those skilled in the art will understand that this disclosure, although described in connection with surgical robotic systems, may also be adapted for use with handheld surgical instruments (such as, for example, endoscopic surgical instruments and/or open surgical instruments) or any other suitable surgical instruments.

Figure 1:
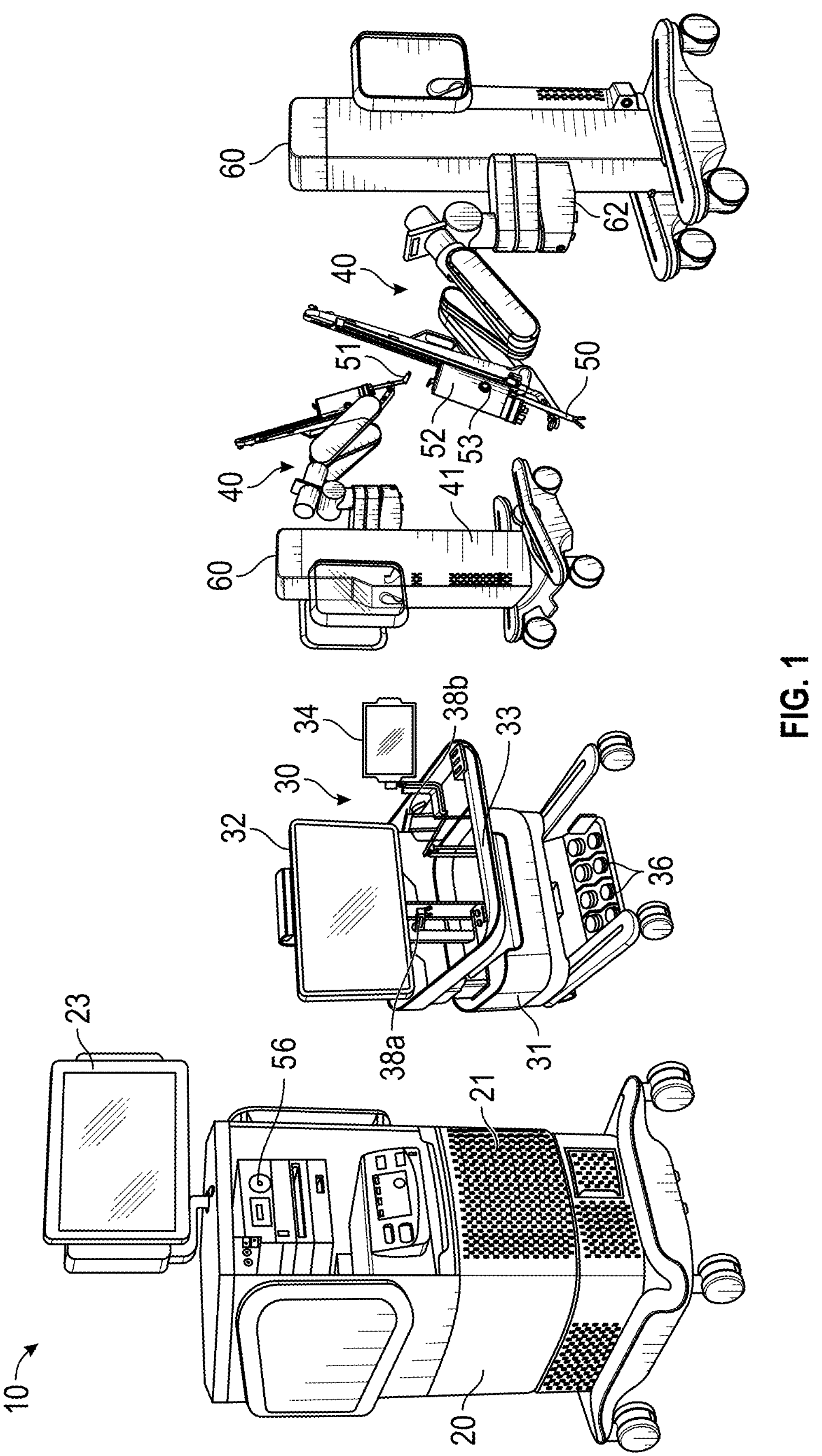
FIG. 1 is a schematic illustration of a surgical robotic system including a control tower, a console, and one or more surgical robotic arms according to aspects of this disclosure.

With reference to FIG. 1, a surgical robotic system 10 includes a control tower 20, which is connected to the components of surgical robotic system 10 including a surgical console 30 and one or more movable carts 60. Each of the movable carts 60 includes a robotic arm 40 having a surgical instrument 50 removably coupled thereto. The robotic arms 40 is also coupled to the movable cart 60. The robotic system 10 may include any number of movable carts 60 and/or robotic arms 40.

The one or more surgical instruments 50 may be configured for use during minimally invasive surgical procedures and/or open surgical procedures. In aspects, one of the surgical instruments 50 may be an endoscope, such as an endoscope camera 51, configured to provide a video feed for the user. In further aspects, one of the surgical instruments 50 may be an energy based surgical instrument such as, for example, an electrosurgical forceps or ultrasonic sealing and dissection instrument configured to seal tissue by grasping tissue (under suitable grasping force) between opposing structures and applying electrosurgical energy or ultrasonic energy, respectively, thereto. In yet further aspects, one of the surgical instruments 50 may be a surgical stapler including a pair of jaws configured to clamp tissue, deploy a plurality of tissue fasteners, e.g., staples, through the clamped tissue, and/or to cut the stapled tissue.

One of the robotic arms 40 may include endoscopic camera 51 configured to capture video of the surgical site. Endoscopic camera 51 may be a stereoscopic endoscope configured to capture two side-by-side (i.e., left and right) images of the surgical site to produce a video stream of the surgical scene. Endoscopic camera 51 is coupled to a video processing device 56, which may be disposed on or within the control tower 20. Video processing device 56 may be any computing device configured to receive the video feed from endoscopic camera 51, perform image processing based on, for example, depth estimating algorithms, and to output the processed video stream for display.

Surgical console 30 includes a first display 32, which displays a video feed of the surgical site provided by camera 51 of surgical instrument 50 disposed on the robotic arms 40, and a second display 34, which displays a user interface for controlling surgical robotic system 10. First and second displays 32 and 34 are touchscreens allowing for displaying various graphical user inputs.

Surgical console 30 also includes a plurality of user interface devices, such as foot pedals 36 and a pair of handle controllers 38*a* and 38*b* which are used by a user to remotely control robotic arms 40. Surgical console 30 further includes an armrest 33 used to support clinician's arms while operating handle controllers 38*a* and 38*b*.

Control tower 20 includes a display 23, which may be a touchscreen, and outputs on the graphical user interfaces (GUIs). Control tower 20 also acts as an interface between surgical console 30 and one or more robotic arms 40. In particular, control tower 20 is configured to control robotic arms 40, such as to move robotic arms 40 and corresponding surgical instrument 50, based on a set of programmable instructions and/or input commands from surgical console 30, in such a way that robotic arms 40 and surgical instrument 50 execute a desired movement sequence in response to input from foot pedals 36 and/or handle controllers 38*a* and 38*b*.

Each of control tower 20, surgical console 30, and robotic arm 40 includes a respective computer 21, 31, 41. Computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area network, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth® (an open wireless protocol for exchanging data over short distances, using short length radio waves, from fixed and mobile devices, creating personal area networks (PANs)), ZigBee® (a specification for a suite of high level communication protocols using small, low-power digital radios based on the IEEE 122.15.4-2003 standard for wireless personal area networks (WPANs)).

Computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
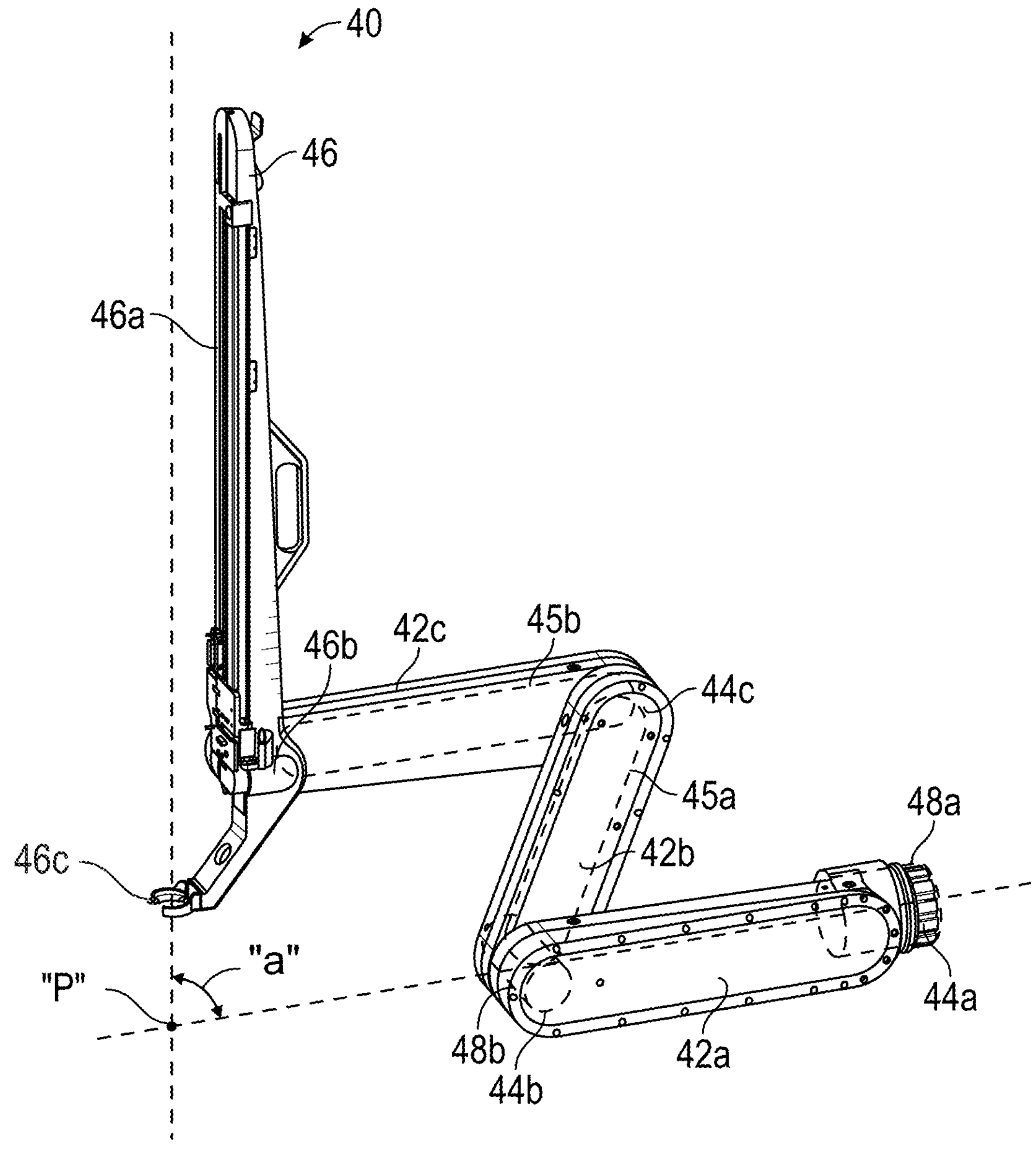
FIG. 2 is a perspective view of a surgical robotic arm of the surgical robotic system of FIG. 1 according to aspects of this disclosure.
Figure 3:
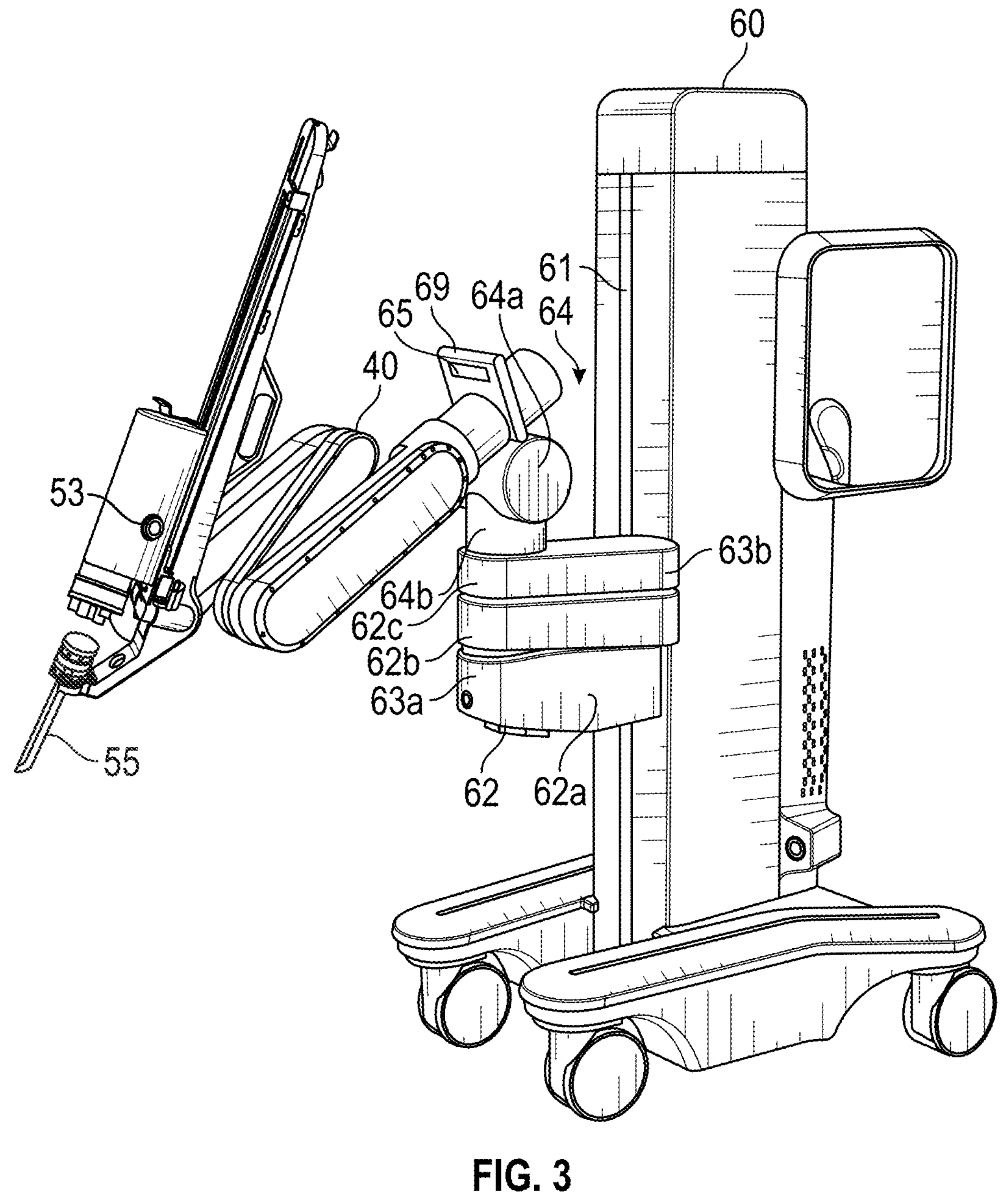
FIG. 3 is a perspective view of a setup arm with the surgical robotic arm of the surgical robotic system of FIG. 1 according to aspects of this disclosure.

With reference to FIG. 2, each of the robotic arms 40 may include a plurality of links 42*a*, 42*b*, 42*c*, which are interconnected at joints 44*a*, 44*b*, 44*c*, respectively. Other suitable configurations of links and joints are also contemplated. Joint 44*a* is configured to secure robotic arm 40 to movable cart 60 and defines a first longitudinal axis. With reference to FIG. 3, movable cart 60 includes a lift 61 and a setup arm 62, which provides a base for mounting of robotic arm 40. Lift 61 allows for vertical movement of setup arm 62. Movable cart 60 also includes a display 69 for displaying information pertaining to the robotic arm 40.

Setup arm 62 includes a first link 62*a*, a second link 62*b*, and a third link 62*c*, which provide for lateral maneuverability of robotic arm 40. Links 62*a*, 62*b*, 62*c* are interconnected at joints 63*a* and 63*b*, each of which may include an actuator (not shown) for rotating links 62*b* and 62*b* relative to each other and link 62*c*. In particular, links 62*a*, 62*b*, 62*c* are movable in their corresponding lateral planes that are parallel to each other, thereby allowing for extension of robotic arm 40 relative to the patient (e.g., surgical table). In aspects, robotic arm 40 may be coupled to the surgical table (not shown). Setup arm 62 includes controls 65 for adjusting movement of links 62*a*, 62*b*, 62*c* as well as lift 61.

Third link 62*c* includes a rotatable base 64 having two degrees of freedom. In particular, rotatable base 64 includes a first actuator 64*a* and a second actuator 64*b*. First actuator 64*a* is rotatable about a first stationary arm axis which is perpendicular to a plane defined by third link 62*c* and second actuator 64*b* is rotatable about a second stationary arm axis which is transverse to the first stationary arm axis. First and second actuators 64*a* and 64*b* allow for full three-dimensional orientation of robotic arm 40.

With reference again to FIG. 2, robotic arm 40 also includes a holder 46 defining a second longitudinal axis and configured to receive an instrument drive unit (IDU) 52 (FIG. 1). IDU 52 is configured to couple to an actuation mechanism of surgical instrument 50 and/or endoscopic camera 51 and is configured to move (e.g., rotate) and actuate instrument 50 and/or camera 51. IDU 52 transfers actuation forces from its actuators to surgical instrument 50 to actuate components (e.g., end effectors) of surgical instrument 50. Holder 46 includes a sliding mechanism 46*a*, which is configured to move IDU 52 along the second longitudinal axis defined by holder 46. Holder 46 also includes a joint 46*b*, which rotates holder 46 relative to link 42*c*. During endoscopic procedures, for example, instrument 50 may be inserted through an endoscopic access port 55 (FIG. 3) held by holder 46. Holder 46 also includes a port latch 46*c* for securing access port 55 (FIG. 3) to holder 46.

Robotic arm 40 also includes a plurality of manual override buttons 53 (FIG. 1) disposed on IDU 52 and/or setup arm 62, which may be used in a manual mode. The user may press one or of buttons 53 to move the component (s) associated with that/those button(s) 53.

Joints 44*a* and 44*b* include actuators 48*a* and 48*b* configured to drive joints 44*a*, 44*b*, 44*c* relative to each other through a series of belts 45*a* and 45*b* or other mechanical linkages such as a drive rod, a cable, or a lever and the like. In particular, actuator 48*a* is configured to rotate robotic arm 40 about a longitudinal axis defined by link 42*a*.

Actuator 48*b* of joint 44*b* is coupled to joint 44*c* via belt 45*a*, and joint 44*c* is in turn coupled to joint 46*c* via belt 45*b*. Joint 44*c* may include a transfer case coupling belts 45*a* and 45*b*, such that actuator 48*b* is configured to rotate each of links 42*b*, 42*c* and holder 46 relative to each other. More specifically, links 42*b*, 42*c*, and holder 46 are passively coupled to the actuator 48*b* which enforces rotation about a remote center point "P" which lies at an intersection of the first axis defined by link 42*a* and the second axis defined by holder 46. Thus, actuator 48*b* controls the angle "a" between the first and second axes allowing for orientation of surgical instrument 50. Due to the interlinking of links 42*a*, 42*b*, 42*c*, and holder 46 via belts 45*a* and 45*b*, the angles between links 42*a*, 42*b*, 42*c* and holder 46 are also adjusted in order to achieve the desired angle "a." In aspects, some or all of joints 44*a*, 44*b*, 44*c* may include an actuator to obviate the need for mechanical linkages.

Figure 4:
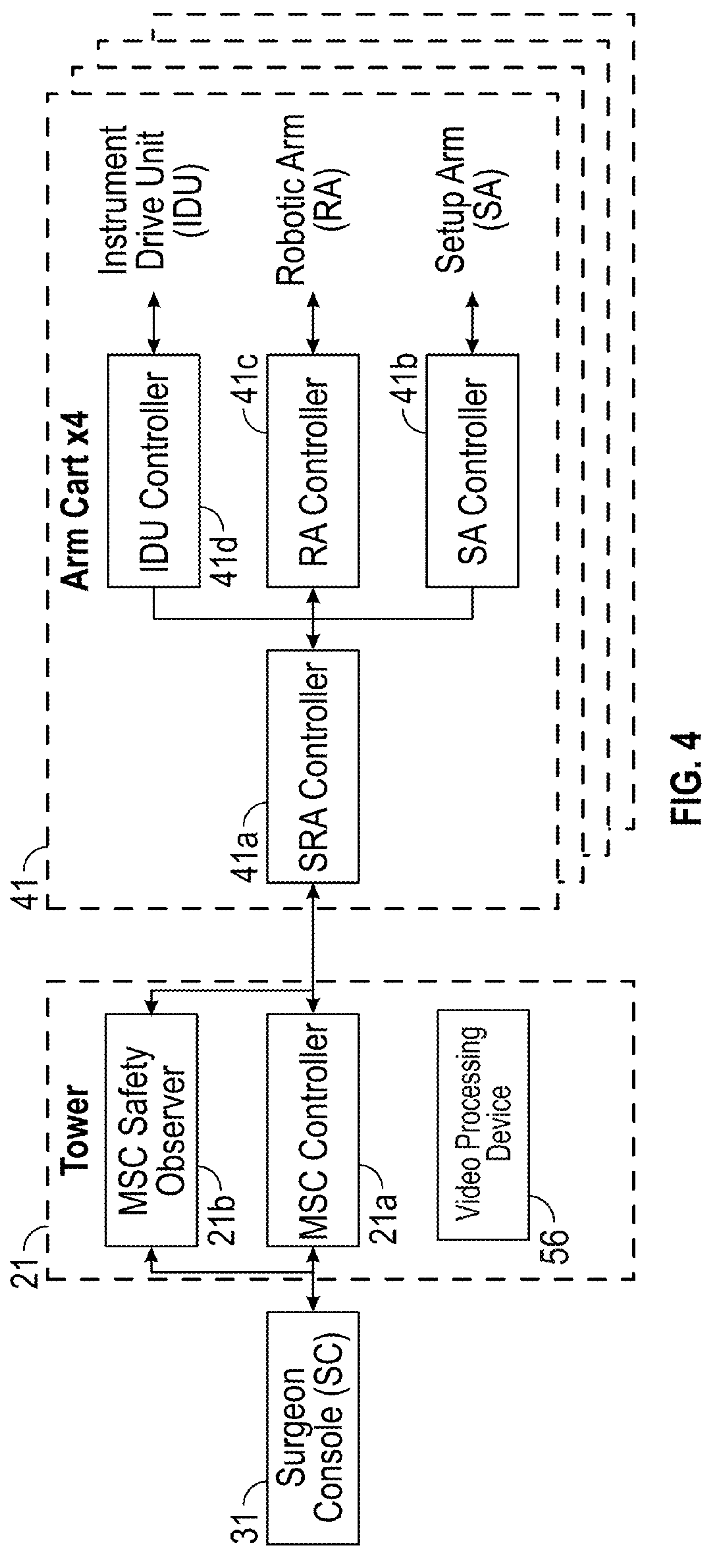
FIG. 4 is a schematic diagram of a computer architecture of the surgical robotic system of FIG. 1 according to aspects of this disclosure.

With reference to FIG. 4, each of the computers 21, 31, 41 of surgical robotic system 10 may include a plurality of controllers, which may be embodied in hardware and/or software. Computer 21 of control tower 20 includes a controller 21*a* and safety observer 21*b*. Controller 21*a* receives data from computer 31 of surgical console 30 about the current position and/or orientation of handle controllers 38*a* and 38*b* and the state of foot pedals 36 and/or other buttons. Controller 21*a* processes these input positions to determine desired drive commands for each joint of robotic arm 40 and/or IDU 52 and communicates these to computer 41 of robotic arm 40. Controller 21*a* also receives back the actual joint angles and uses this information to determine force feedback commands that are transmitted to computer 31 of surgical console 30 to provide haptic feedback through handle controllers 38*a* and 38*b*. Handle controllers 38*a* and 38*b* include one or more haptic feedback vibratory devices that output haptic feedback. Safety observer 21*b* performs validity checks on the data going into and out of controller 21*a* and notifies a system fault handler if errors in the data transmission are detected to place computer 21 and/or surgical robotic system 10 into a safe state.

Computer 41 includes a plurality of controllers, namely, a main cart controller 41*a*, a setup arm controller 41*b*, a robotic arm controller 41*c*, and an IDU controller 41*d*. Main cart controller 41*a* receives and processes joint commands from controller 21*a* of computer 21 and communicates them to setup arm controller 41*b*, robotic arm controller 41*c*, and IDU controller 41*d*. Main cart controller 41*a* also manages instrument exchanges and the overall state of movable cart 60, robotic arm 40, and IDU 52. Main cart controller 41*a*, in addition, communicates actual joint angles to controller 21*a*.

Joints 63*a* and 63*b* and rotatable base 64 of setup arm 62 are passive joints (i.e., no actuators are present therein) allowing for manual adjustment thereof by a user. Joints 63*a* and 63*b* and rotatable base 64 include brakes that are disengaged by the user to configure setup arm 62. Setup arm controller 41*b* monitors slippage of each of joints 63*a* and 63*b* and rotatable base 64, when brakes are engaged or can be freely moved by the operator when brakes are disengaged, but do not impact controls of other joints. Alternatively, setup arm controller 41*b* may control each of joints 63*a* and 63*b* and rotatable base 64 (where joints 63*a* and 63*b* and rotatable base 64 are active joints with actuators), calculate desired motor movement commands (e.g., motor torque) for the pitch axis, and control the brakes.

Robotic arm controller 41*c* controls each joint 44*a* and 44*b* of robotic arm 40 and calculates desired motor torques required for gravity compensation, friction compensation, and closed loop position control of robotic arm 40. Robotic arm controller 41*c* calculates a movement command based on the calculated torque. The calculated motor commands are then communicated to one or more of actuators 48*a* and 48*b* in robotic arm 40. The actual joint positions are then transmitted by actuators 48*a* and 48*b* back to robotic arm controller 41*c*.

IDU controller 41*d* receives desired joint angles for surgical instrument 50, such as wrist and jaw angles, and computes desired currents for the motors in IDU 52. IDU controller 41*d* calculates actual angles based on the motor positions and transmits the actual angles back to main cart controller 41*a*.

Robotic arm 40 is controlled in response to a pose of the handle controller controlling robotic arm 40, e.g., handle controller 38*a*, which is transformed into a desired pose of robotic arm 40 through a hand eye transform function executed by controller 21*a*. The hand eye function, as well as other functions described herein, is/are embodied in software executable by controller 21*a* or any other suitable controller described herein. The pose of handle controller 38*a* may be embodied as a coordinate position and role-pitch-yaw ("RPY") orientation relative to a coordinate reference frame, which is fixed to surgical console 30. The desired pose of instrument 50 is relative to a fixed frame on robotic arm 40. The pose of handle controller 38*a* is then scaled by a scaling function executed by controller 21*a*. In aspects, the coordinate position is scaled down and the orientation is scaled up by the scaling function. In addition, controller 21*a* may execute a clutching function, which disengages handle controller 38*a* from robotic arm 40. In particular, controller 21*a* stops transmitting movement commands from handle controller 38*a* to robotic arm 40 if certain movement limits or other thresholds are exceeded and in essence acts like a virtual clutch mechanism, e.g., limiting mechanical input from effecting mechanical output.

The desired pose of robotic arm 40 is based on the pose of handle controller 38*a* and is then passed by an inverse kinematics function executed by controller 21*a*. The inverse kinematics function calculates angles for joints 44*a*, 44*b*, 44*c* of robotic arm 40 that achieve the scaled and adjusted pose input by handle controller 38*a*. The calculated angles are then passed to robotic arm controller 41*c*, which includes a joint axis controller having a proportional-derivative (PD) controller, the friction estimator module, the gravity compensator module, and a two-sided saturation block, which is configured to limit the commanded torque of the motors of joints 44*a*, 44*b*, 44*c*.

Figure 5:
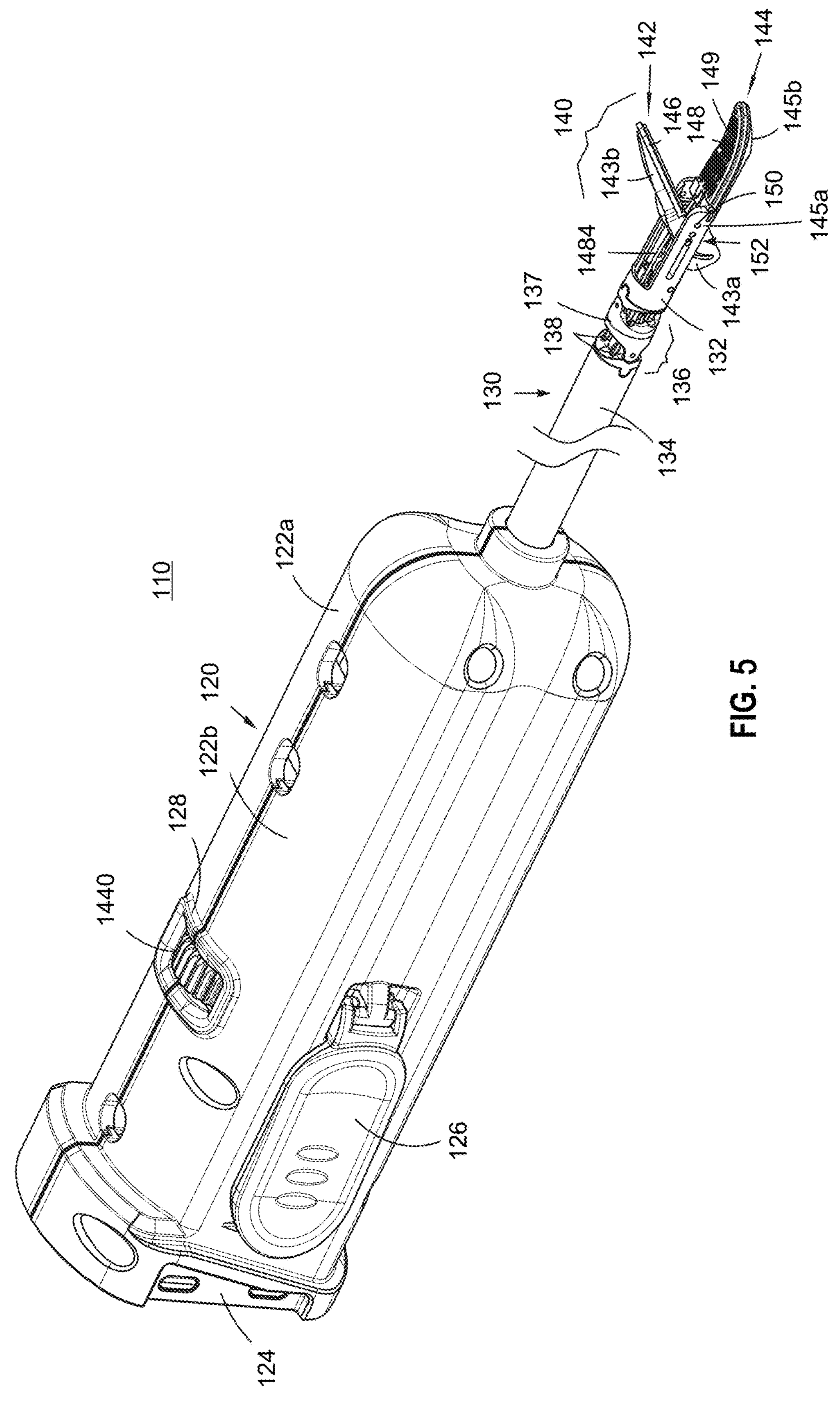
FIG. 5 is a perspective view of a surgical instrument provided in accordance with the present disclosure configured for mounting on a robotic arm of a surgical robotic system such as the surgical robotic system of FIG. 1.
Figure 6A:
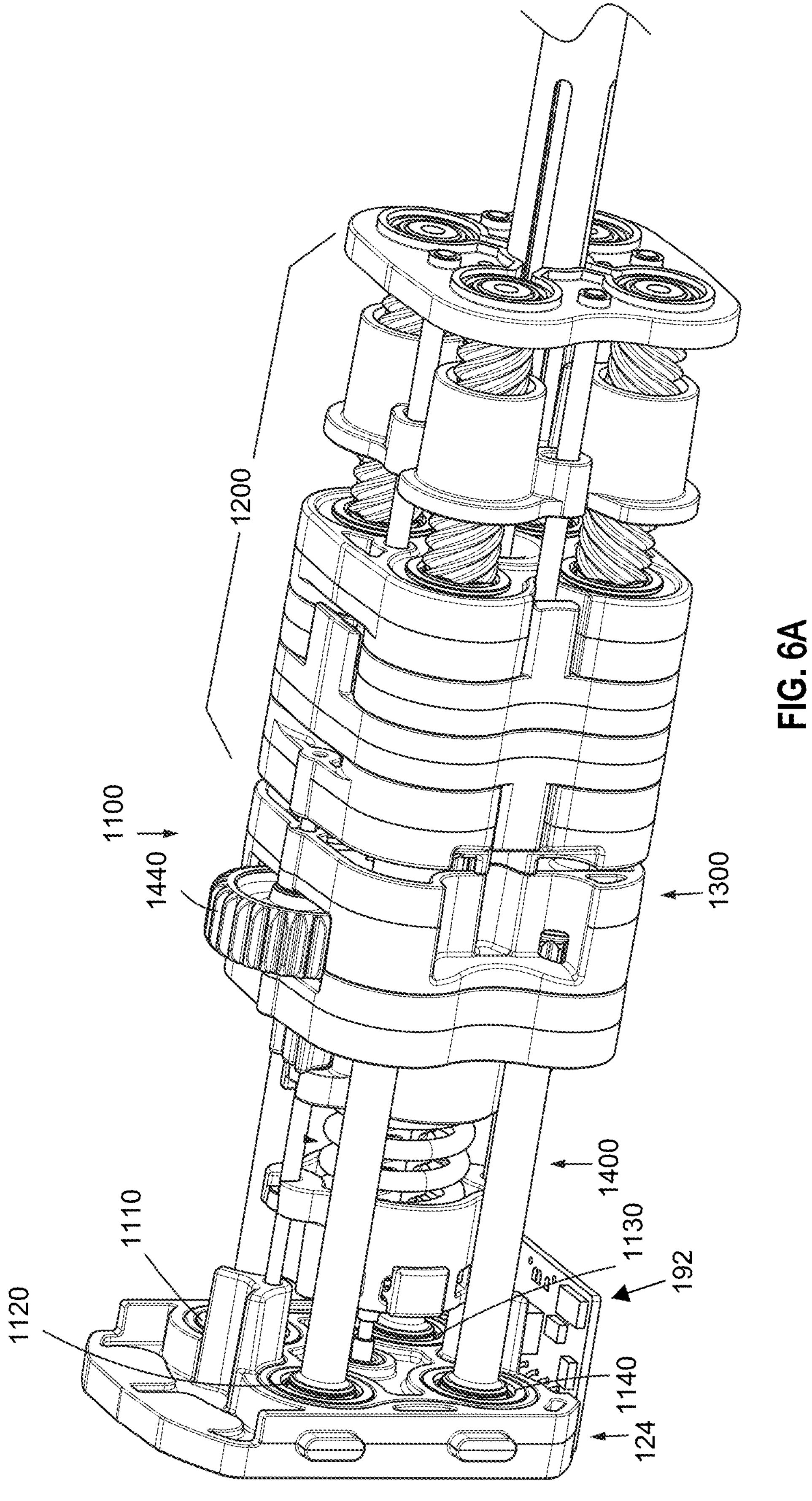
FIGS. 6A and 6B are front and rear perspective views, respectively, of a proximal portion of the surgical instrument of FIG. 5, with an outer shell removed.
Figure 6B:
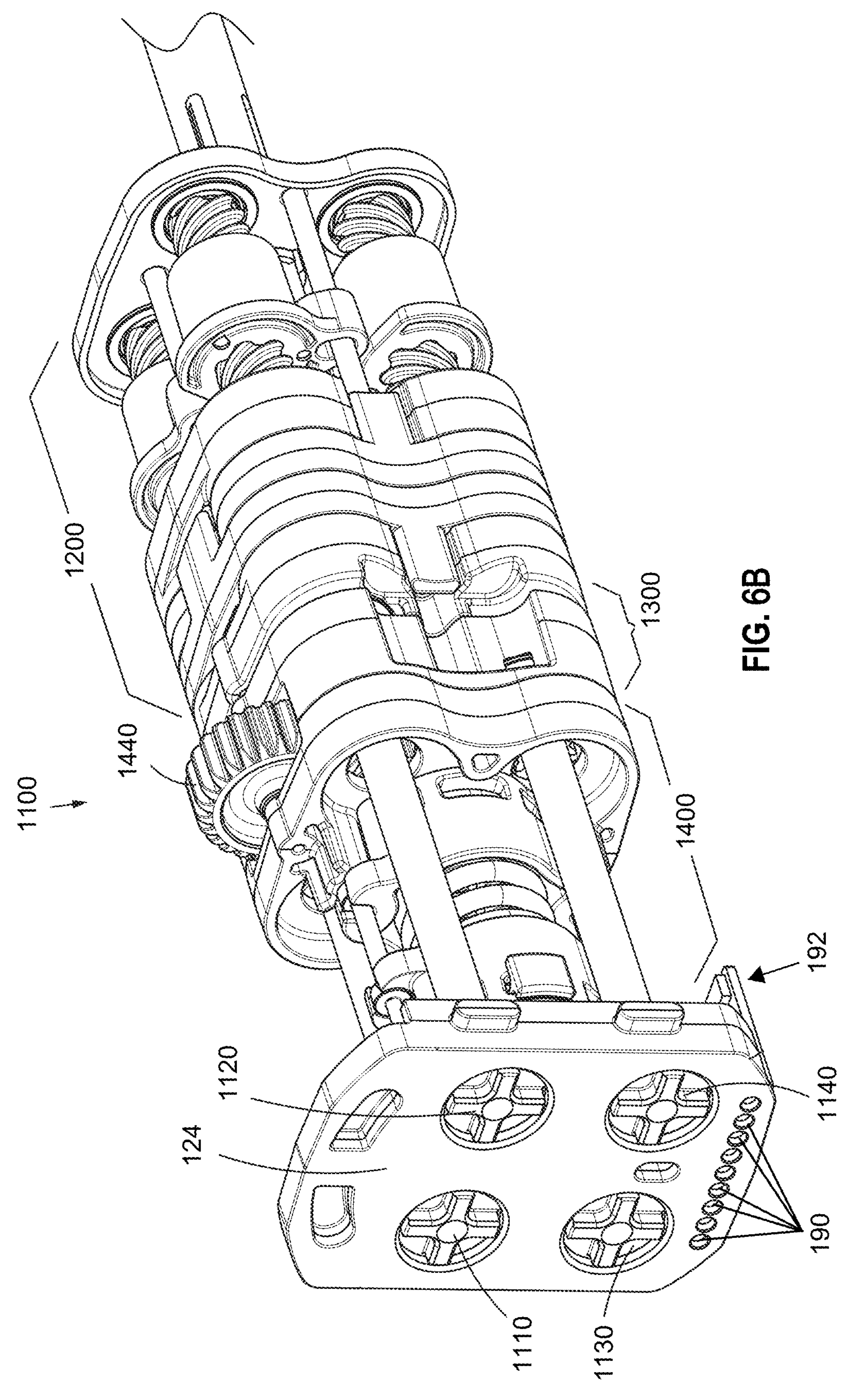
Figure 7:
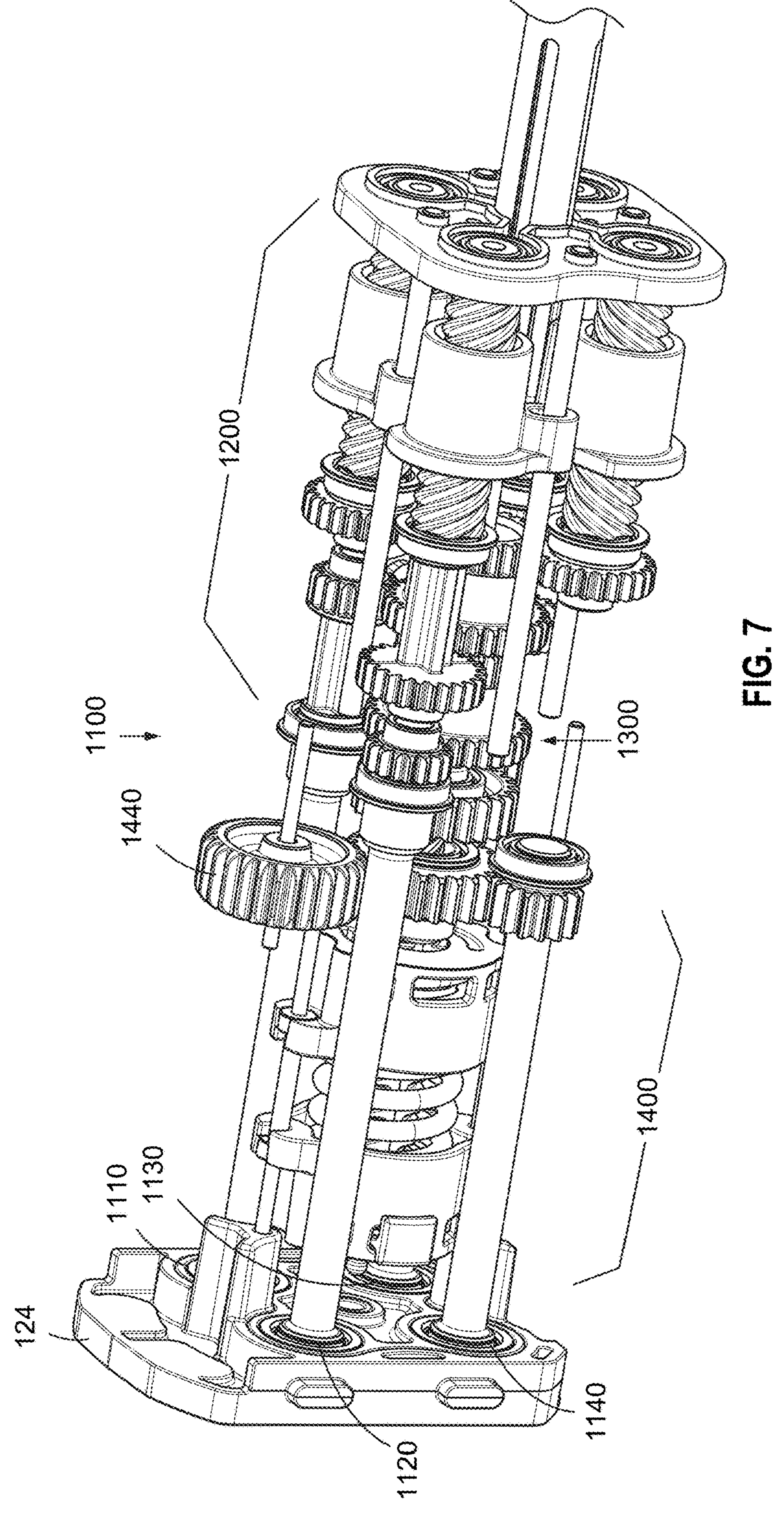
FIG. 7 is a front perspective view of the proximal portion of the surgical instrument of FIG. 5 with the outer shell and additional internal components removed.

Turning to FIGS. 5-7, a surgical instrument 110 provided in accordance with the present disclosure generally includes a housing 120, a shaft 130 extending distally from housing 120, an end effector assembly 140 extending distally from shaft 130, and an actuation assembly 1100 disposed within housing 120 and operably associated with end effector assembly 140. Instrument 110 is detailed herein as an articulating electrosurgical forceps configured for use with a surgical robotic system, e.g., surgical robotic system 10 (FIG. 1). However, the aspects and features of instrument 110 provided in accordance with the present disclosure, detailed below, are equally applicable for use with other suitable surgical instruments, e.g., graspers, staplers, clip appliers, and/or in other suitable surgical systems, e.g., motorized, other power-driven systems, and/or manually-actuated surgical systems (including handheld instruments).

With particular reference to FIG. 5, housing 120 of instrument 110 includes first and second body portions 122*a*, 122*b* and a proximal face plate 124 that cooperate to enclose actuation assembly 1100 therein. Proximal face plate 124 includes through holes defined therein through which input couplers 1110-1140 (FIG. 6B) of actuation assembly 1100 extend. A pair of latch levers 126 (only one of which is illustrated in FIG. 5) extending outwardly from opposing sides of housing 120 enable releasable engagement of housing 120 with a robotic arm of a surgical robotic system, e.g., surgical robotic system 10 (FIG. 1). A window 128 defined through housing 120 permits thumbwheel 1440 to extend therethrough to enable manual manipulation of thumbwheel 1440 from the exterior of housing 120 to permit manual opening and closing of end effector assembly 140.

Referring also to FIGS. 6A-7, a plurality of electrical contacts 190 extend through one or more apertures defined through proximal face plate 124 to enable electrical communication between instrument 110 and surgical robotic system 10 (FIG. 1) when instrument 110 is engaged on a robotic arm thereof, e.g., for the communication of data, control, and/or power signals therebetween. As an alternative to electrical contacts 190 extending through proximal face plate 124, other suitable transmitter, receiver, and/or transceiver components to enable the communication of data, control, and/or power signals are also contemplated, e.g., using RFID, Bluetooth®, WiFi®, or via any other suitable wired, wireless, contacted, or contactless communication method. At least some of the electrical contacts 190 are electrically coupled with electronics 192 mounted on an interior side of proximal face plate 124, e.g., within housing 120. Electronics 192 may include, for example, a storage device, a communications device (including suitable input/output components), and a CPU including a memory and a processor. Electronics 192 may be mounted on a circuit board or otherwise configured, e.g., as a chip.

The storage device of electronics 192 stores information relating to surgical instrument such as, for example: the item number, e.g., SKU number; date of manufacture; manufacture location, e.g., location code; serial number; lot number; use information; setting information; adjustment information; calibration information; security information, e.g., encryption key(s), and/or other suitable additional or alternative data. The storage device of electronics 192 may be, for example, a magnetic disk, flash memory, optical disk, or other suitable data storage device.

As an alternative or in addition to storing the above noted information in the storage device of electronics 192, some or all of such information, e.g., the use information, calibration information, setting information, and/or adjustment information, may be stored in a storage device associated with surgical robotic system 10 (FIG. 1), a remote server, a cloud server, etc., and accessible via instrument 110 and/or surgical robotic system 10 (FIG. 1). In such configurations, the information may, for example, be updated by manufacturer provided updates, and/or may be applied to individual instruments, units of instruments (e.g., units from the same manufacturing location, manufacturing period, lot number, etc.), or across all instruments. Further still, even where the information is stored locally on each instrument, this information may be updated by manufacturer provided updates manually or automatically upon connection to the surgical robotic system 10 (FIG. 1).

Referring again to FIG. 5, shaft 130 of instrument 110 includes a distal segment 132, a proximal segment 134, and an articulating section 136 disposed between the distal and proximal segments 132, 134, respectively. Articulating section 136 includes one or more articulating components 137, e.g., links, joints, etc. A plurality of articulation cables 138, e.g., four (4) articulation cables, or other suitable actuators, extend through articulating section 136. More specifically, articulation cables 138 are operably coupled to distal segment 132 of shaft 130 at the distal ends thereof and extend proximally from distal segment 132 of shaft 130, through articulating section 136 of shaft 130 and proximal segment 134 of shaft 130, and into housing 120, wherein articulation cables 138 operably couple with an articulation sub-assembly 1200 of actuation assembly 1100 (FIG. 6A) to enable selective articulation of distal segment 132 (and, thus end effector assembly 140) relative to proximal segment 134 and housing 120, e.g., about at least two axes of articulation (yaw and pitch articulation, for example). Articulation cables 138 are arranged in a generally rectangular configuration, although other suitable configurations are also contemplated. In some configurations, as an alternative, shaft 130 is substantially rigid, malleable, or flexible and not configured for active articulation. Articulation sub-assembly 1200 is described in greater detail below.

With respect to articulation of end effector assembly 140 relative to proximal segment 134 of shaft 130, actuation of articulation cables 138 may be accomplished in pairs. More specifically, in order to pitch end effector assembly 140, the upper pair of cables 138 are actuated in a similar manner while the lower pair of cables 138 are actuated in a similar manner relative to one another but an opposite manner relative to the upper pair of cables 138. With respect to yaw articulation, the right pair of cables 138 are actuated in a similar manner while the left pair of cables 138 are actuated in a similar manner relative to one another but an opposite manner relative to the right pair of cables 138. Other configurations of articulation cables 138 or other articulation actuators are also contemplated.

Continuing with reference to FIG. 5, end effector assembly 140 includes first and second jaw members 142, 144, respectively. Each jaw member 142, 144 includes a proximal flange portion 143*a*, 145*a* and a distal body portion 143*b*, 145*b*, respectively. Distal body portions 143*b*, 145*b* define opposed tissue contacting surfaces 146, 148, respectively. Proximal flange portions 143*a*, 145*a* are pivotably coupled to one another about a pivot 150 and are operably coupled to one another via a cam slot assembly 152 including a cam pin slidably received within cam slots defined within the proximal flange portion 143*a*, 145*a* of at least one of the jaw members 142, 144, respectively, to enable pivoting of jaw member 142 relative to jaw member 144 and distal segment 132 of shaft 130 between a spaced apart position (e.g., an open position of end effector assembly 140) and an approximated position (e.g., a closed position of end effector assembly 140) for grasping tissue between tissue contacting surfaces 146, 148. As an alternative to this unilateral configuration, a bilateral configuration may be provided whereby both jaw members 142, 144 are pivotable relative to one another and distal segment 132 of shaft 130. Other suitable jaw actuation mechanisms are also contemplated.

In configurations, a longitudinally extending knife channel 149 (only knife channel 149 of jaw member 144 is illustrated; the knife channel of jaw member 142 is similarly configured) is defined through the tissue contacting surface 146, 148 of one or both jaw members 142, 144. In such aspects, a knife assembly including a knife rod (not shown) extending from housing 120 through shaft 130 to end effector assembly 140 and a knife (not shown, see knife 290 of end effector assembly 240 (FIG. 8)) disposed within end effector assembly 140 between jaw members 142, 144 is provided. The knife is selectively translatable through the knife channel(s) 149 and between the jaw member 142, 144 to cut tissue grasped between tissue contacting surfaces 146, 148 of jaw members 142, 144, respectively. The knife rod is operably coupled to a knife drive sub-assembly 1300 (FIG. 7) of actuation assembly 1100 (FIGS. 6A-6B) at a proximal end thereof to enable the selective actuation of the knife rod to, in turn, reciprocate the knife between jaw members 142, 144 to cut tissue grasped between tissue contacting surfaces 146, 148. As an alternative to a longitudinally advanceable mechanical knife, other suitable mechanical cutters are also contemplated, e.g., guillotine style cutters, as are energy based cutters, e.g., RF electrical cutters, ultrasonic cutters, etc., in static or dynamic configurations.

Referring still to FIG. 5, a drive rod 1484 is operably coupled to cam slot assembly 152 of end effector assembly 140, e.g., engaged with the cam pin thereof, such that longitudinal actuation of drive rod 1484 pivots jaw member 142 relative to jaw member 144 between the spaced apart and approximated positions. More specifically, urging drive rod 1484 proximally pivots jaw member 142 relative to jaw member 144 towards the approximated position while urging drive rod 1484 distally pivots jaw member 142 relative to jaw member 144 towards the spaced apart position. However, other suitable mechanisms and/or configurations for pivoting jaw member 142 relative to jaw member 144 between the spaced apart and approximated positions in response to selective actuation of drive rod 1484 are also contemplated. Drive rod 1484 extends proximally from end effector assembly 140 through shaft 130 and into housing 120 wherein drive rod 1484 is operably coupled with a jaw drive sub-assembly 1400 of actuation assembly 1100 (FIGS. 6A-6B) to enable selective actuation of end effector assembly 140 to grasp tissue therebetween and apply a jaw force within an appropriate jaw force range.

Tissue contacting surfaces 146, 148 of jaw members 142, 144, respectively, are at least partially formed from an electrically conductive material and are energizable to different potentials to enable the conduction of RF electrical energy through tissue grasped therebetween, although tissue contacting surfaces 146, 148 may alternatively be configured to supply any suitable energy, e.g., thermal, microwave, light, ultrasonic, ultrasound, etc., through tissue grasped therebetween for energy based tissue treatment. Instrument 110 defines a conductive pathway (not shown) through housing 120 and shaft 130 to end effector assembly 140 that may include lead wires, contacts, and/or electrically conductive components to enable electrical connection of tissue contacting surfaces 146, 148 of jaw members 142, 144, respectively, to an energy source (not shown), e.g., an electrosurgical generator, for supplying energy to tissue contacting surfaces 146, 148 to treat, e.g., seal, tissue grasped between tissue contacting surfaces 146, 148.

With additional reference to FIGS. 6A-7, as noted above, actuation assembly 1100 is disposed within housing 120 and includes an articulation sub-assembly 1200, a knife drive sub-assembly 1300, and a jaw drive sub-assembly 1400. Articulation sub-assembly 1200 is operably coupled between first and second input couplers 1110, 1120, respectively, of actuation assembly 1100 and articulation cables 138 (FIG. 5) such that, upon receipt of appropriate inputs into first and/or second input couplers 1110, 1120, articulation sub-assembly 1200 manipulates cables 138 (FIG. 5) to articulate end effector assembly 140 in a desired direction, e.g., to pitch and/or yaw end effector assembly 140. Articulation sub-assembly 1200 is described in greater detail below.

Knife drive sub-assembly 1300 is operably coupled between third input coupler 1130 of actuation assembly 1100 and the knife rod such that, upon receipt of appropriate input into third input coupler 1130, knife drive sub-assembly 1300 manipulates the knife rod to reciprocate the knife between jaw members 142, 144 to cut tissue grasped between tissue contacting surfaces 146, 148.

Jaw drive sub-assembly 1400 is operably coupled between fourth input coupler 1140 of actuation assembly 1100 and drive rod 1484 such that, upon receipt of appropriate input into fourth input coupler 1140, jaw drive sub-assembly 1400 pivots jaw members 142, 144 between the spaced apart and approximated positions to grasp tissue therebetween and apply a jaw force within an appropriate jaw force range.

Actuation assembly 1100 is configured to operably interface with a surgical robotic system, e.g., system 10 (FIG. 1), when instrument 110 is mounted on a robotic arm thereof, to enable robotic operation of actuation assembly 1100 to provide the above detailed functionality. That is, surgical robotic system 10 (FIG. 1) selectively provides inputs, e.g., rotational inputs to input couplers 1110-1140 of actuation assembly 1100 to articulate end effector assembly 140, grasp tissue between jaw members 142, 144, and/or cut tissue grasped between jaw members 142, 144. However, as noted above, it is also contemplated that actuation assembly 1100 be configured to interface with any other suitable surgical systems, e.g., a manual surgical handle, a powered surgical handle, etc.

Figures 8, 9A, 9B:
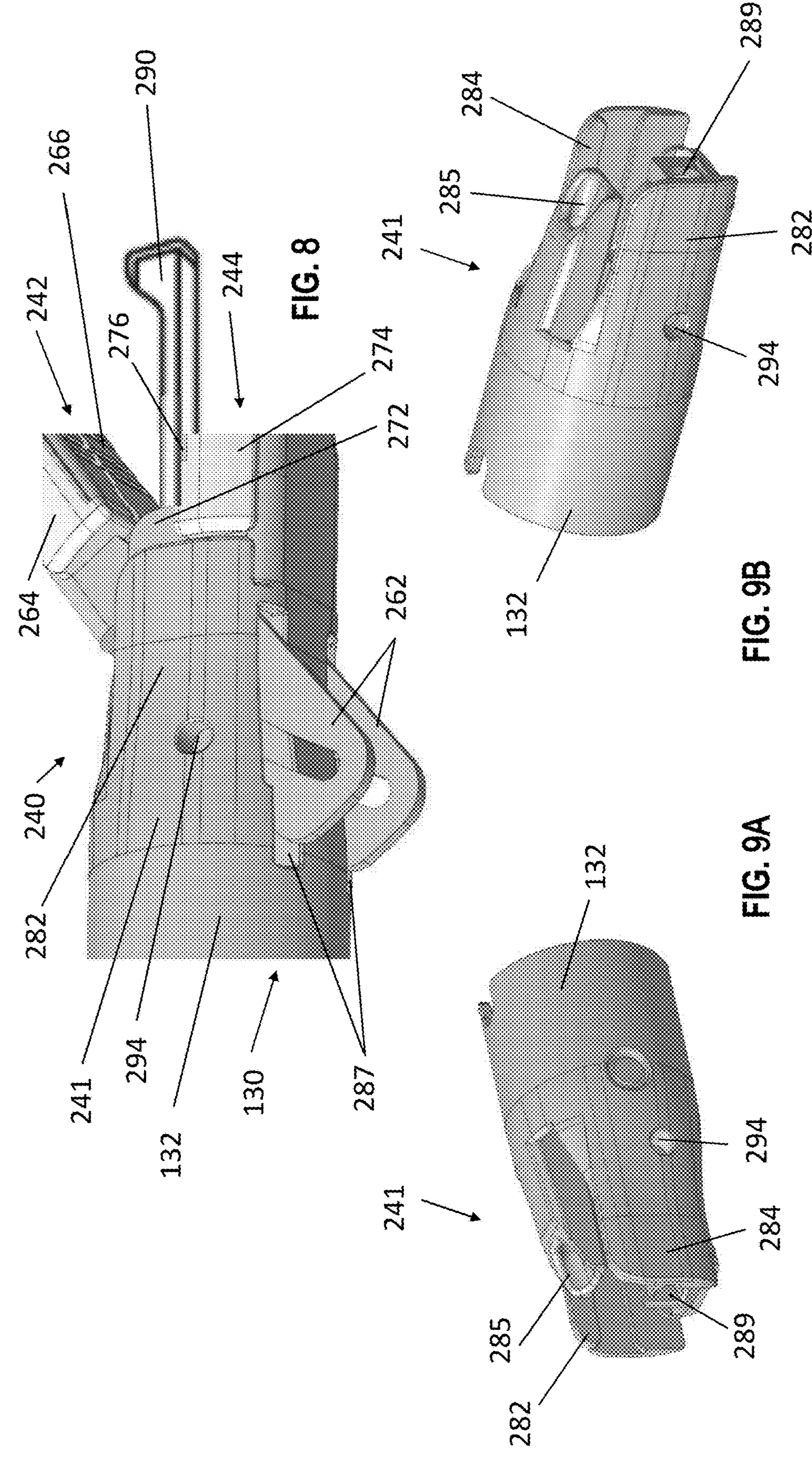
FIG. 8 is a perspective view of a proximal portion of another end effector assembly provided in accordance with this disclosure configured for use with the surgical instrument of FIG. 5 or any other suitable surgical instrument.
FIGS. 9A and 9B are first and second perspective side views, respectively, of the clevis of the end effector assembly of FIG. 8.

Turning to FIG. 8, another end effector assembly provided in accordance with the present disclosure and configured for use with surgical instrument 110 (FIG. 5) or any other suitable surgical instrument is shown generally identified by reference numeral 240. End effector assembly 240 is similar to and may include any of the features of end effector assembly 140 (FIG. 5), and/or may be utilized as part of surgical instrument 110 (FIGS. 5-7) similarly as described above with respect to end effector assembly 140 (FIG. 5), except as explicitly contradicted below.

End effector assembly 240 includes a clevis 241 joined to or forming distal segment 132 of shaft 130 of instrument 110 (see also FIG. 5) and first and second jaw members 242, 244, respectively, operably coupled to clevis 241. More specifically, first jaw member 242 is pivotably coupled to clevis 241 and second jaw member 244, while second jaw member 244 is fixed relative to clevis 241. Each jaw member 242, 244 includes a proximal flange portion 262, 272, and a distal body portion 264, 274 that supports an opposed electrically conductive tissue contacting surface 266, 276, respectively.

Proximal flange portions 262, 272 of jaw members 242, 244 are pivotably coupled to one another about a pivot (not shown, the pivot is internal to clevis 241 and may be a single pin, split pin, multiple pins, or other pivot structure extending through corresponding pivot apertures defined within proximal flange portions 262, 272), and are operably coupled to one another via a cam assembly (not shown, the cam assembly is internal to clevis 241 and may include, for example, a cam pin slidably received within cam slots defined within proximal flange portions 262, 272 of at least one of jaw members 242, 244, respectively) to enable pivoting of jaw member 242 relative to jaw member 244 and clevis 241 between a spaced apart position (e.g., an open position of end effector assembly 240) and an approximated position (e.g., a closed position of end effector assembly 240) for grasping tissue between electrically conductive tissue contacting surfaces 266, 276. As an alternative to this unilateral configuration, a bilateral configuration may be provided whereby both jaw members 242, 244 are pivotable relative to one another and clevis 241. Any suitable jaw actuation mechanism such as, for example, using a push-pull drive bar as detailed above, may be utilized to actuate jaw member(s) 242, 244.

Electrically conductive tissue contacting surfaces 266, 276 of jaw members 242, 244, respectively, are at least partially formed from an electrically conductive material and are energizable to different potentials to enable the conduction of RF electrical energy through tissue grasped therebetween, although electrically conductive tissue contacting surfaces 266, 276 may alternatively be configured to supply any suitable energy, e.g., thermal, microwave, light, ultrasonic, ultrasound, etc., through tissue grasped therebetween for energy based tissue treatment. In order to enable the conduction of energy to and from electrically conductive tissue contacting surfaces 266, 276, electrical lead wires and/or other suitable electrical conductors (not shown) electrically connect to electrically conductive tissue contacting surfaces 266, 276 within jaw members 242, 244 and extend proximally therefrom through clevis 241, shaft 130 of instrument 110, and into housing 120 (see FIG. 5) for ultimate connection to an energy source (not shown), e.g., an electrosurgical generator, to enable the supply of energy to electrically conductive tissue contacting surfaces 266, 276 to treat, e.g., seal, tissue grasped therebetween.

With additional reference to FIGS. 9A and 9B, clevis 241, as noted above, is joined to or forms distal segment 132 of shaft 130 of instrument 110 (see also FIG. 5) and internally supports the pivot and/or cam structures (e.g., pins) that operably couple first and second jaw members 242, 244 to one another and clevis 241. Further, clevis 241 retains proximal flange portion 262, 272 of jaw members 242, 244 between spaced-apart arms 282, 284 thereof. More specifically, first jaw member 242 is pivotably coupled to clevis 241 and second jaw member 244 between spaced-apart arms 282, 284, while second jaw member 244 is fixed relative to clevis 241 between spaced-apart arms 282, 284. Clevis 241 may further include various support and/or guide structures such as, for example, a lead wire channel 285, proximal flange slots 287 for the bifurcated proximal flange portion 262 of pivotable first jaw member 242, a knife guide 289 for guiding knife 290, and/or other suitable features.

Continuing with reference to FIGS. 8-9B, clevis 241 further includes one or more locating features 294 disposed and/or defined on outwardly-facing surfaces of each of spaced-apart arms 282, 284 of clevis 241. As shown, locating features 294 are defined as recesses within outwardly-facing surfaces of arms 282, 284, although alternative or additional locating features 294 are also contemplated such as, for example: protrusions, ramps, slots, pegs, channels, rails, combinations thereof, etc. Locating features 294 are aligned with one another such that an axis defined through locating features 294 of arms 282, 284 extends substantially perpendicularly relative to a longitudinal axis defined through clevis 241.

Figure 10:
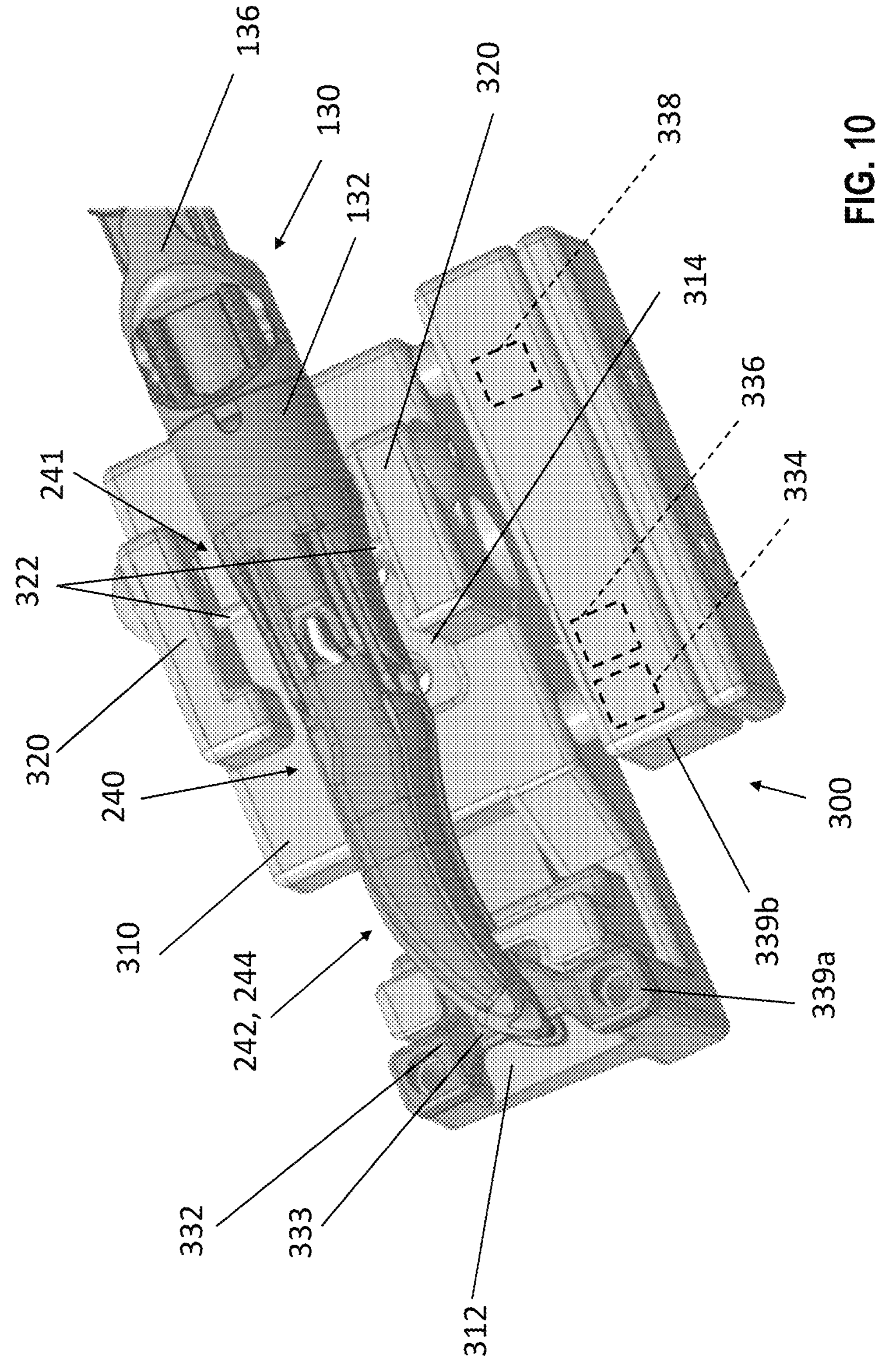
FIG. 10 is a perspective view of the end effector assembly of FIG. 8 attached to the surgical instrument of FIG. 5 and secured within a fixture to facilitate testing and/or calibration of the surgical instrument in accordance with this disclosure.

With additional reference to FIG. 10, locating features 294 of clevis 241 of end effector assembly 240 enable proper alignment and engagement of end effector assembly 240 within a fixture 300. Fixture 300 includes a base 310 defining a jaw-receiving area 312 and a clevis-receiving area 314, first and second supports 320 disposed on base 310 on either side of clevis-receiving area 314, and a plurality of test sensors such as, for example, a jaw force sensor 332, a jaw spacing sensor 334, a knife detection sensor 336, an articulation sensor 338, etc. Other suitable sensors are also contemplated such as, for example, a thermal camera, thermal sensor, and/or any other suitable sensor configured to measure performance, position, alignment, temperature, force, etc.

Jaw force sensor 332 may include a load cell 333 positionable between jaw members 242, 244 and/or any other suitable components to enable detection of a pressure and/or force applied between jaw members 242, 244.

Jaw spacing sensor 334 may be configured to detect a linear gap between jaw members 242, 244 at one or more known positions along the lengths thereof and/or may be configured to detect an angle defined between jaw members 242, 244. Jaw spacing sensor 334 may include, for example, a camera, laser, and/or other suitable optics or other components to enable jaw gap and/or jaw angle detection.

Knife detection sensor 336 may be configured to detect the presence, position, travel path, and/or speed of knife 290 before, prior to, or as knife 290 is deployed between jaw members 242, 244. Knife detection sensor 336 may include, for example, a camera, laser, and/or other suitable optics or other components to enable detection of one or more of the above or other properties of knife 290. Knife detection sensor 336 may be separate from jaw spacing sensor 334 or knife detection sensor 336 and jaw spacing sensor 334 may be integrated into the same sensing components.

Articulation direction sensor 338 may include, for example, a gyroscope, accelerometer, magnetometer, and/or other suitable orientation and/or position sensor configured to enable detection of the orientation and/or position of end effector assembly 240, e.g., rotationally, in a yaw direction, in a pitch direction, etc.

As an alternative to including all sensors 332, 334, 336, 338 on a single fixture 300, various different fixtures 300 may be provided similarly as detailed herein except that each fixture may include one or more of sensors 332, 334, 336, 338. Further still, fixture 300 may be configured for receiving interchangeable sensor modules, e.g., a first sensor module 339*a* and a second sensor module 339*b*, each including one or more of sensors 332, 334, 336, 338. Alternative or additional sensors may also be provided on fixture 300, a different fixture, or in an interchangeable module for use with fixture 300. Thus, any suitable test or combinations of tests may be performed using one or more fixtures 300 each configured to ensure proper alignment and engagement of end effector assembly 240 therein, as detailed below.

Referring still to FIGS. 8-10, as noted above, first and second supports 320 are disposed on base 310 on either side of clevis-receiving area 314 thereof. First and second supports 320 may each include a retention feature 322 such as, for example, a pin, configured for alignment and engagement with the corresponding locating feature 294 of clevis 241. As an alternative to pins, retention features 322 may include recesses, ramps, slots, channels, rails, combinations thereof, etc. and/or any other suitable complementary structures configured for alignment and engagement with locating feature 294 of clevis 241. Retention features 322 may be fixed, spring loaded, deployable, or otherwise configured to facilitate alignment and secure engagement of end effector assembly 240 within fixture 300 upon positioning end effector assembly 240 therein. The alignment and engagement between retention features 322 and locating features 294 ensures precise and proper positioning and orientation of end effector assembly 240 relative to test sensors 332, 334, 336, 338 throughout actuation, articulation, and/or other movement of end effector assembly 240 to thereby facilitate accurate testing of end effector assembly 240. This may be particularly important where precise measurements and/or sensitive test sensors are utilized such as, for example, in sensing jaw force, jaw spacing, knife detection, articulation, etc. More specifically, the dedicated structural locating features 294 of end effector assembly 240 facilitate securing and aligning end effector assembly 240 within fixture 300 and overcome the challenges associated with securing and aligning end effector assembly 240 (throughout actuation, articulation, and/or other movement of end effector assembly 240) in the absence of such dedicated structures. Further, fixture 300 is disposed distally of articulating section 136 of shaft 130 and the engagement of fixture 300 with end effector assembly 240 does not interfere with articulating section 136 of shaft 130 or other actuation of end effector assembly 240. In this manner, fixture 300 may be utilized to facilitate testing of various features of end effector assembly 240 at various different articulated positions of end effector assembly 240, as detailed below with reference to FIG. 11.

Figure 11:
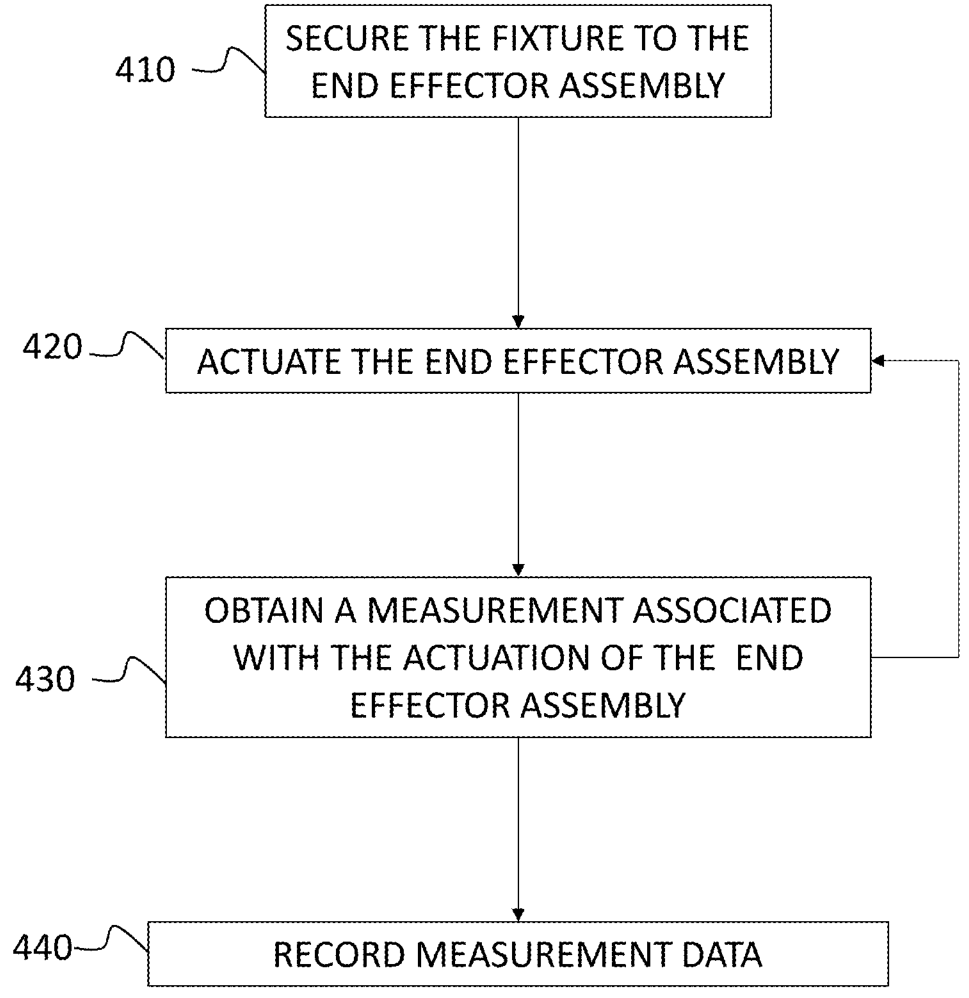
FIG. 11 is a flow diagram illustrating a method of testing and/or calibration in accordance with this disclosure.

Turning to FIG. 11, in conjunction with FIGS. 8-10, as noted above, various tests may be performed on end effector assembly 240 using one or more fixtures 300. For example, with respect to method 400, in order to perform one or more tests on end effector assembly 240, fixture 300 is first secured to end effector assembly 240, e.g., as detailed above, such that end effector assembly 240 is secured relative to the one or more test sensors 332, 334, 336, 338 in proper alignment therewith, as indicated in step 410.

With fixture 300 secured to end effector assembly 240 at step 410, the method proceeds to step 420, wherein end effector assembly 240 is actuated. Actuation of end effector assembly 240 may include, for example, one or more of: rotating end effector assembly 240 to a desired orientation, articulating end effector assembly 240 to a desired position, pivoting jaw member 242 to the open or closed position (or other position therebetween) relative to jaw member 244, deploying knife 290 between jaw members 242, 244, etc.

During and/or after the actuation of end effector assembly 240, one or more measurements associated with the actuation of end effector assembly 240 is obtained, as indicated at step 430. The measurement(s) may be obtained using one or more of sensors 332, 334, 336, 338 and may include, for example: a jaw pressure or force measurement indicating a pressure or force applied to a structure, e.g., load cell 333, disposed between jaw members 242, 244 in the closed position thereof using sensor 332; a jaw gap measurement indicating one or more linear gap distances between jaw members 242, 244 and/or a jaw angle between jaw members 242, 244 in the open, closed, or any other position thereof using sensor 334; a knife measurement indicating a position, speed, travel path, etc. of knife 290 between jaw members 242, 244 using sensor 336; and/or an articulation measurement indicating a position and/or orientation of end effector assembly 240, e.g., rotationally, in a yaw direction, in a pitch direction, etc., relative to shaft 130 using sensor 338. With respect to articulation, as an alternative to pitch and yaw, reference may be made to Polar Coordinates such as, for example, to reference radial distance, inclination (elevation), and azimuth.

After the measurement(s) are obtained in step 430, step 420 and step 430 may be sequentially repeated any suitable number of times to obtain appropriate measurement(s). For example: jaw pressure or force measurements may be obtained for various different actuations of jaw members 242, 244 and/or at various different rotational and/or articulated positions of end effector assembly 240; jaw gap measurements may be obtained for various different actuations of jaw members 242, 244 and/or at various different rotational and/or articulated positions of end effector assembly 240; knife measurements may be obtained for various different actuations of knife 290 and/or jaw members 242, 244, and/or at various different rotational and/or articulated positions of end effector assembly 240; and/or articulation measurements may be obtained for various different actuations of rotation and/or articulation of end effector assembly 240.

The measurement(s) obtained in step(s) 430 may be recorded at step 440. If necessary, the measurement(s) may be processed, e.g., used to calculate reference data, calibration data, pass/fail data, etc., individually or together with additional measurement or other data, prior to recording at step 440. Recording the measurement(s) at step 440, whether processed or recoded as raw data, may include, for example: recording whether end effector assembly 240 passes post-manufacture testing, writing reference and/or calibration data to the storage device of electronics 192 (FIG. 6A) for calibration and/or compensation during use (e.g., to ensure accurate operation regardless of manufacturing variations and/or variations due to the rotated and/or articulated position of end effector assembly 240), for gathering test data as part or research and development efforts, etc.

Recorded jaw pressure or force measurement data may be utilized, for example, to ensure a pressure or force within an appropriate range is applied by end effector assembly 240, for calibration of the actuation of jaw members 242, 244 necessary to achieve a target pressure or force (or range thereof), and/or to enable compensation mapping to adjust actuation of jaw members 242, 244 to achieve a desired jaw pressure or force (or jaw pressure or force with a desired range) regardless of the rotational and/or articulated position of end effector assembly 240. This compensation mapping may be done, for example, using one or more equations or in any other suitable manner.

Recorded jaw gap measurement data may be utilized, for example, to determine how far the jaw members 242, 244 can be opened during use (and, in aspects, how far the jaw members 242, 244 can be opened during use in various different rotational and/or articulated positions). As other examples, jaw gap measurement data may be utilized for calibration of the actuation of jaw members 242, 244 necessary to achieve a target closed or open jaw position, and/or for compensation mapping to adjust actuation of jaw members 242, 244 to achieve a desired open and/or closed jaw gap regardless of the rotational and/or articulated position of end effector assembly 240.

Recorded knife measurement data may be utilized, for example, for calibration to determine a fully retracted position, fully extended position, speed, and/or other properties of knife 290 for a given amount of actuation thereof, to enable determination of the positon of knife 290 for a given amount of actuation thereof, and/or for compensation mapping to ensure proper deployment of knife 290 regardless of the rotational and/or articulated position of end effector assembly 240. This compensation mapping may be done, for example, using one or more equations or in any other suitable manner.

Recorded articulation measurement data may be utilized, for example, for calibration to enable determination of an actual orientation and/or position of end effector assembly 240 in response to a given actuation thereof, for compensation, and/or to ensure that minimally acceptable rotational and/or orientations positions are attainable.

Referring generally to FIGS. 8-11, as detailed above, one or more of sensors 332, 334, 336, 338 may be configured to determine: a jaw pressure or force; a jaw gap and/or jaw angle; a knife position, speed, travel path, etc.; an articulation position and/or orientation; etc. Sensors 332, 334, 336, 338 and/or other suitable sensors associated with fixture 300 may additionally or alternatively be utilized to determine, for example, an articulation center point for the articulation of end effector assembly 240 and/or a maximum jaw angle, position, or plane associated with an open-most position of jaw members 242, 244.

Fixture 300 may be engaged with end effector assembly 240 as detailed hereinabove and utilized to perform one or more of the tests detailed above or any other suitable test at one or more different times and/or for one or more different purposes. For example, testing using fixture 300 may be performed at manufacturing or post-manufacture testing (e.g., prior to attachment with a surgical robot to perform a surgical procedure); in anticipation of use (e.g., after attachment with the surgical robot to perform the surgical procedure but prior to insertion through a trocar); during use (e.g., at the trocar, within the trocar, or within the patient); in between uses or after use (e.g., after withdrawal from the trocar); upon occurrence of an event (e.g., a user-request for calibration, detection of an error, etc.); and/or in any other suitable manner. Testing using fixture 300 may be performed for the purpose(s) of: data collection; quality/acceptability/performance testing; calibration (including re-calibration, compensation mapping, etc.); troubleshooting; and/or for other purposes.

The raw and/or processed test data obtained from testing may be stored, as noted above, in the storage device of electronics 192 (FIG. 6A), a storage device associated with surgical robotic system 10 (FIG. 1), a remote server, a cloud server, etc. The data may be accessible and/or utilized by instrument 110 (FIG. 5) (and/or other instruments), surgical robotic system 10 (FIG. 1) (and/or other surgical robotic systems), a remote server, a cloud server, etc. for various purposes including, for example, to set or modify use settings (e.g., of the instrument(s) and/or the surgical robotic system(s)), to build and/or refine calibration models (e.g., equations), to set and/or modify manufacturing settings, and/or for other purposes.

Figure 12:
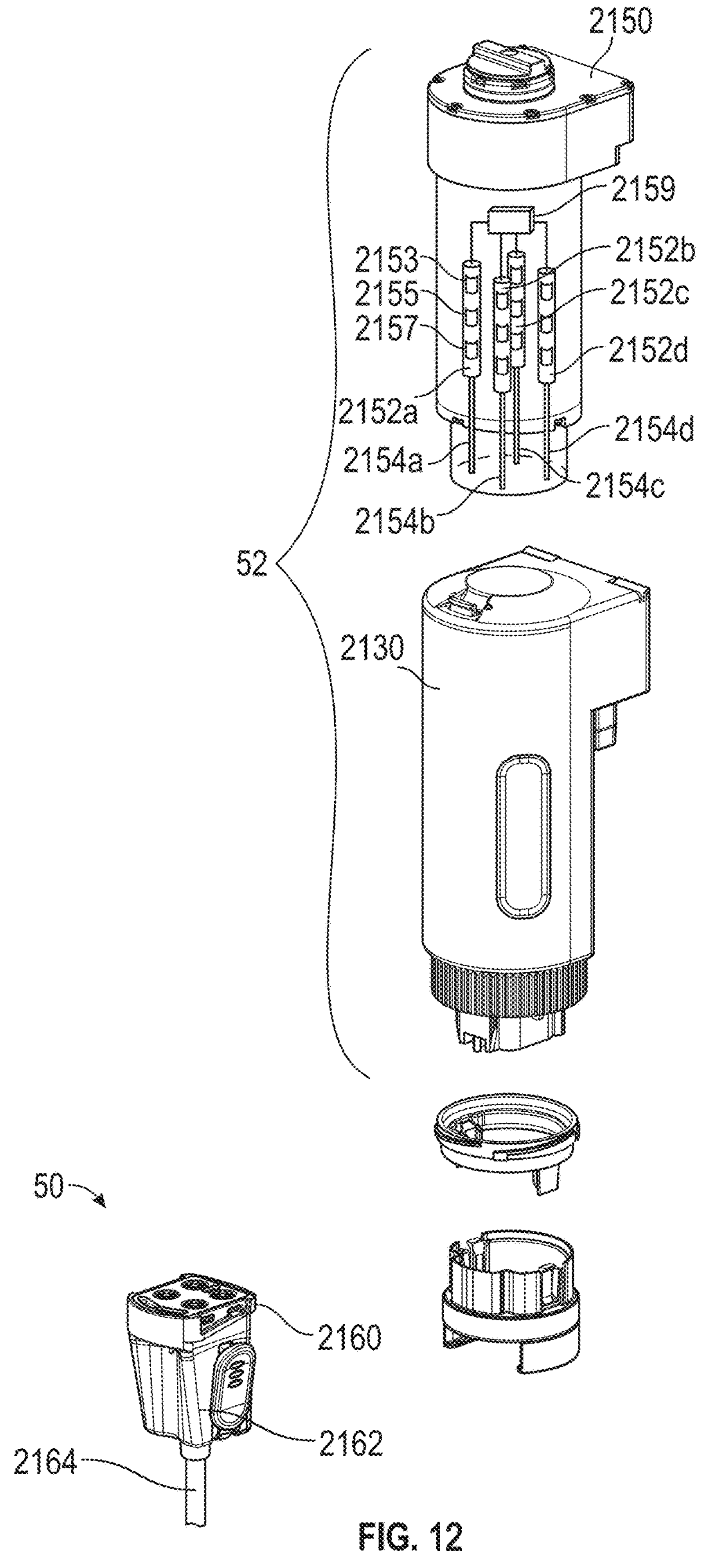
FIG. 12 is a perspective view, with parts separated, of an instrument drive unit (IDU) and a surgical instrument according to aspects of this present disclosure.

With reference to FIG. 12, IDU 52 of surgical robotic system 10 is shown in more detail. IDU 52 is configured to transfer power and actuation forces from its motors 2152*a*, 2152*b*, 2152*c*, 2152*d* to an attached surgical instrument (e.g., surgical instrument 50) to drive movement of components (e.g., cable drives, gears, pulleys, friction wheels, rack and pinion arrangements, etc.) of the surgical instrument 50 to effect articulation, rotation, pitch, yaw, clamping, cutting, and/or any other suitable function(s) of the surgical instrument 50. Although described herein with respect to surgical instrument 50, it is understood that IDU 52 may connect to and operate any other suitable surgical instrument such as, for example, surgical instrument 110 (FIG. 5).

IDU 52 includes a motor pack 2150 and a sterile barrier housing 2130. Motor pack 2150 includes motors 2152*a*, 2152*b*, 2152*c*, 2152*d* for controlling various operations of instrument 50, as noted above. Instrument 50 is removably couplable to IDU 52. As motors 2152*a*, 2152*b*, 2152*c*, 2152*d* of motor pack 2150 are actuated, rotation of drive transfer shafts 2154*a*, 2154*b*, 2154*c*, 2154*d* of motors 2152*a*, 2152*b*, 2152*c*, 2152*d*, respectively, is transferred to the corresponding drive assemblies of instrument 50.

Instrument 50, similarly as detailed above with respect to surgical instrument 110 (FIG. 5), for example, or in any other suitable manner, is configured to transfer rotational forces/movement supplied by IDU 52 (e.g., via motors 2152*a*, 2152*b*, 2152*c*, 2152*d* of motor pack 2150) into longitudinal movement or translation of the cables or drive shafts to effect various functions of an end effector 2200 (FIG. 13) of instrument 50.

Each motor 2152*a*, 2152*b*, 2152*c*, 2152*d* includes a current sensor 2153, a torque sensor 2155, and an encoder sensor 2157. For conciseness only operation of motor 2152*a* is described below; motors 2152*b*, 2152*c*, 2152*d* operate in the same manner. Sensors 2153, 2155, 2157 monitor the performance of motor 2152*a*. Current sensor 2153 is configured to measure the current draw of motor 2152*a* and torque sensor 2155 is configured to measure motor torque. Torque sensor 2155 may be any force or strain sensor including one or more strain gauges configured to convert mechanical forces and/or strain into a sensor signal indicative of the torque output by motor 2152*a*. Encoder 2157 may be any device that provides a sensor signal indicative of the number of rotations of motor 2152*a*, such as a mechanical encoder or an optical encoder. Parameters which are measured and/or determined by encoder 2157 may include speed, distance, revolutions per minute, position, and the like. The sensor signals from sensors 2153, 2155, 2157 are transmitted to IDU controller 41*d* (FIG. 4), which then controls motors 2152*a*, 2152*b*, 2152*c*, 2152*d* based on the sensor signals. In particular, motors 2152*a*, 2152*b*, 2152*c*, 2152*d* are controlled by an actuator controller 2159, which controls torque outputted and angular velocity of motors 2152*a*, 2152*b*, 2152*c*, 2152*d*. In aspects, additional position sensors may also be used, which include, but are not limited to, potentiometers coupled to movable components and configured to detect travel distances, Hall Effect sensors, accelerometers, and gyroscopes. In aspects, a single controller can perform the functionality of IDU controller 41*d* and actuator controller 2159.

Continuing with reference to FIG. 12, instrument 50 includes an adapter 2160 having a housing 2162 at a proximal end portion thereof and an elongated shaft 2164 that extends distally from housing 2162. Housing 2162 of instrument 50 is configured to selectively couple to IDU 52 to enable motors 2152*a*, 2152*b*, 2152*c*, 2152*d* of IDU 52 to operate the end effector 2200 (FIG. 13) of instrument 50. Housing 2162 of instrument 50, more specifically, supports a drive assembly that mechanically and/or electrically cooperates with motors 2152*a*, 2152*b*, 2152*c*, 2152*d* of IDU 52, e.g., as detailed above with respect to surgical instrument 110 (FIG. 5) or in any other suitable manner. The drive assembly of instrument 50 may include any suitable electrical and/or mechanical component to effectuate driving force/movement.

Figure 13:
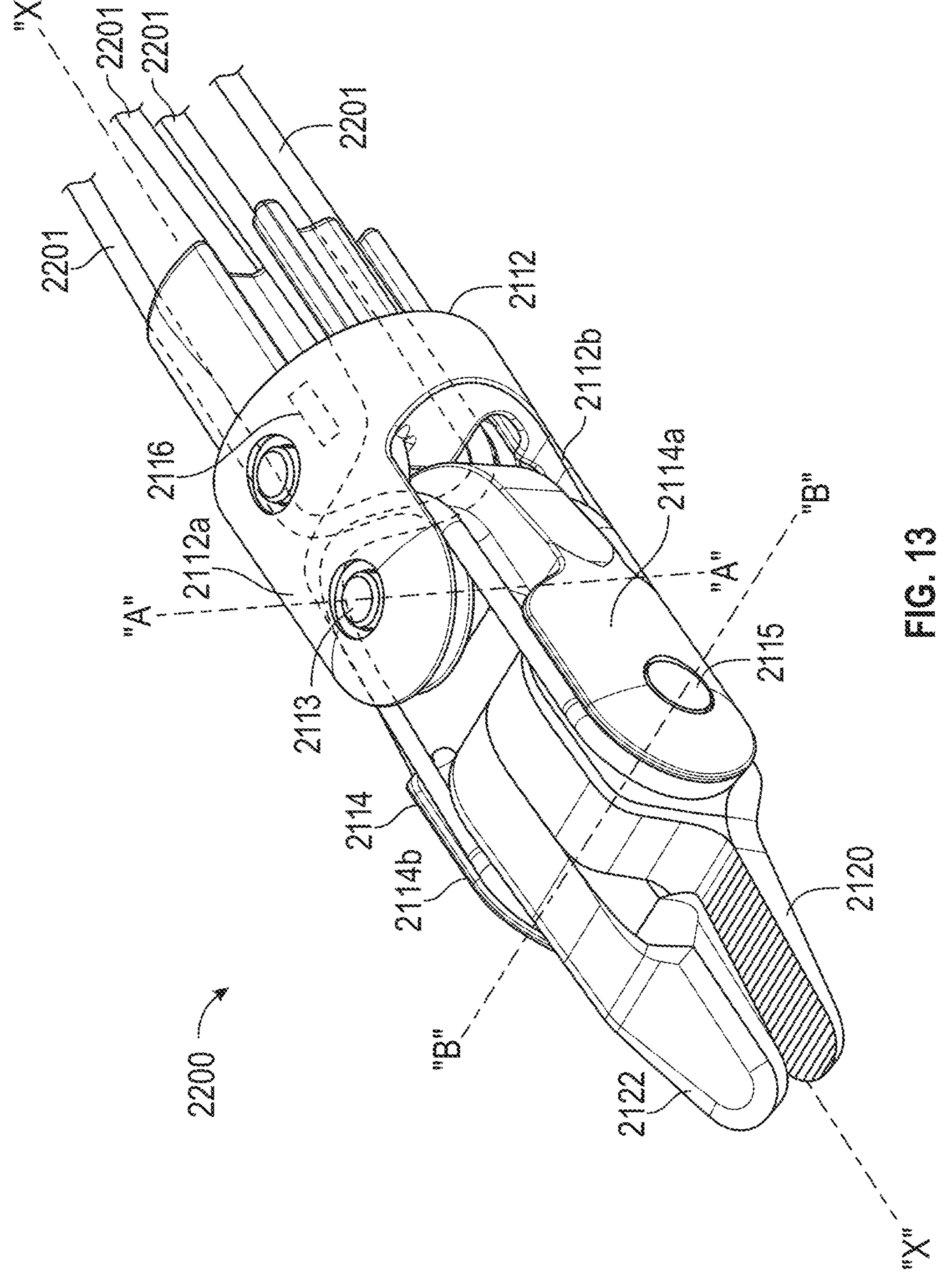
FIG. 13 is a top, perspective view of an end effector assembly, according to aspects of this disclosure, for use in the surgical robotic system of FIG. 1.

Referring also to FIG. 13, instrument 50 also includes an end effector assembly 2200 coupled to elongated shaft 2164. End effector assembly 2200 may include any number of degrees of freedom allowing end effector assembly 2200 to articulate, pivot, etc., relative to elongated shaft 2164. End effector assembly 2200 may be any suitable surgical end effector assembly configured to treat tissue, such as a dissector, grasper, sealer, stapler, etc. As shown in FIG. 13, end effector assembly 2200 may include a pair of opposing jaw members 2120 and 2122 either or both of which is movable relative to the other. As shown in FIG. 13, both jaw members 2120 and 2122 are movable relative to each other.

In aspects, end effector assembly 2200 may include a proximal portion 2112 having a first pin 2113 and a distal portion 2114. End effector assembly 2200 may be actuated using a plurality of cables 2201 routed through proximal and distal portions 2112 and 2114 around their respective pulleys 2112*a*, 2112*b*, 2114*a*, 2114*b*, which are integrally formed as arms of the proximal and distal portions 2112 and 2114. In aspects, end effector assembly 2200 and, more specifically, distal portion 2114 and jaw members 2120 and 2122 thereof, may be articulated about the axis "A-A" to control a yaw angle of end effector assembly 2200 with respect to a longitudinal axis "X-X." Distal portion 2114 includes a second pin 2115; jaw members 2120 and 2122 are pivotably coupled to second pin 2115. Jaw members 2120 and 2122 are configured to pivot about an axis "B-B" defined by second pin 2115 allowing for controlling a pitch angle of jaw members 2120 and 2122 as well as opening and closing of jaw members 2120 and 2122. The yaw, pitch, and jaw angles are controlled by adjusting the tension and/or length and direction (e.g., proximal or distal) of cables 2201. End effector assembly 2200 may also include a cable displacement sensor 2116 configured to measure position of cables 2201. In these or other aspects, end effector assembly 2200 may have three degrees of freedom: yaw, pitch, and jaw angle between jaw members 2120 and 2122.

Figure 14:
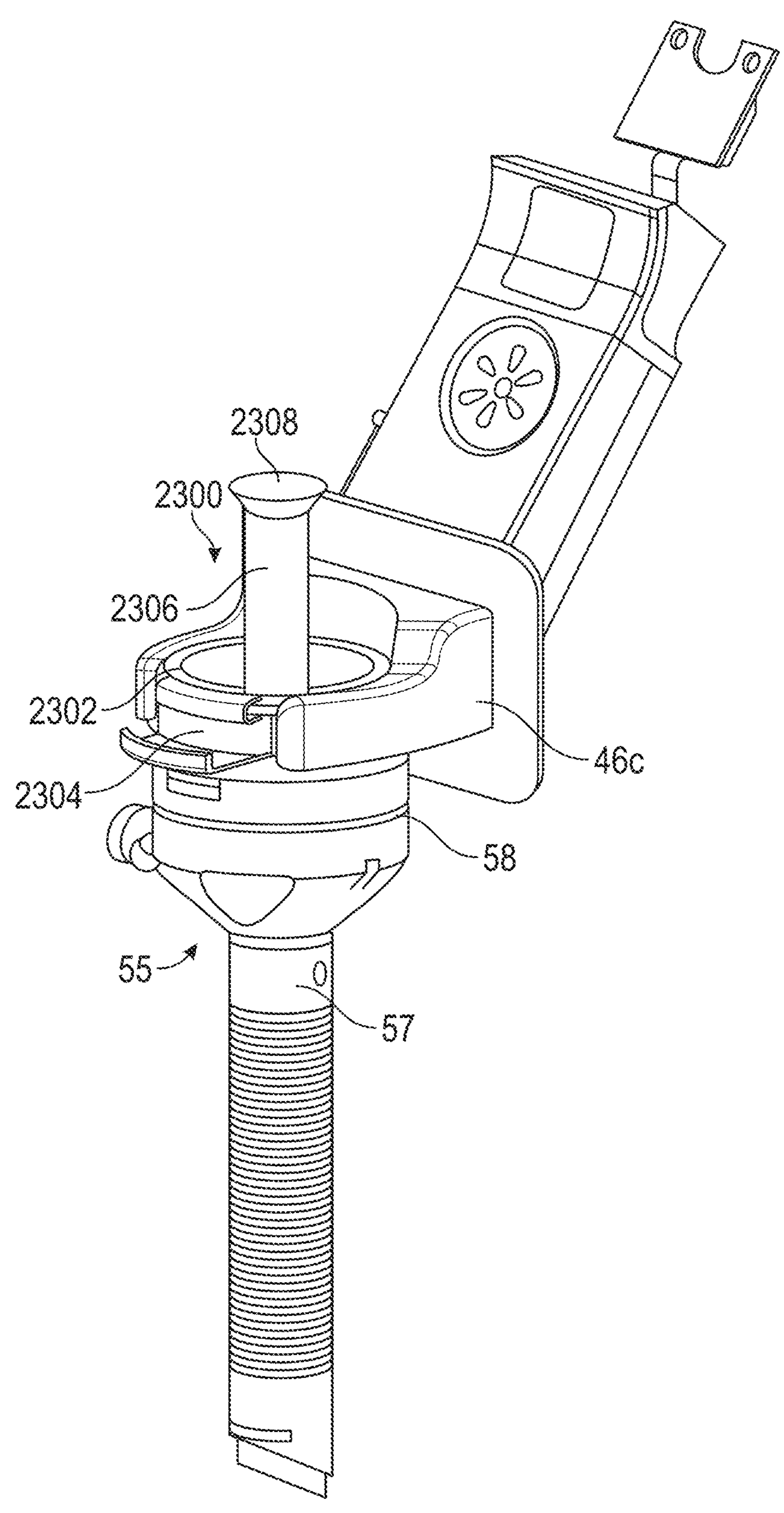
FIG. 14 is a perspective view of a calibration attachment according to aspects of this disclosure.

Continuing with reference to FIGS. 12 and 13, calibration of instrument 50 is performed after coupling instrument 50 to IDU 52 of the robotic arm 40 (FIGS. 2 and 3). Calibration is performed for each of the degrees of freedom, e.g., yaw, pitch, and jaw angle between jaw members 2120 and 2122 and may be accomplished by moving end effector assembly 2200 about each of the axes "A-A" and "B-B" as well as opening and/or closing jaw members 2120 and 2122 between two limits of the corresponding motion range. Calibration may be performed within an access port 55 (FIG. 14). Referring also to FIG. 14, access port 55 may include a cannula 57 configured to be inserted into a patient and a seal housing 58 enclosing one or more seals and valves for coupling to insufflation equipment. Cannula 57 may provide mechanical limits for calibrating end effector assembly 2200. In particular, moving end effector assembly 2200 and/or jaw members 2120 and 2122 thereof during calibration until contacting the inner surface of cannula 57 may be used as mechanical limits, i.e., end stops. During yaw calibration, end effector assembly 2200 is pivoted about the "A-A" axis in either direction until end effector assembly 2200 reaches the end stop by hitting the inner surface of cannula 57. Reaching an end stop may be detected by torque sensor(s) 2155 of the motors **2152*a*, 2152*b*, 2152*c*, and/or 2152*d*. Pitch calibration is performed similarly to yaw calibration, except that end effector assembly 2200 is pivoted about the "B-B" axis. Jaw angle calibration is performed by moving, e.g., opening, jaw members 2120 and 2122 until each of the jaw members 2120 and 2122 hits the inner surface of cannula 57**.

Access ports 55 of various diameters, which can range from 5 mm to about 15 mm, are used during laparoscopic surgical procedures. Larger access ports may be used with larger instruments and/or smaller instruments. However, larger access ports provide different limits during calibration for smaller instruments than if smaller access ports were utilized for calibration of the smaller instruments. A calibration attachment 2300 in accordance with this disclosure may thus be utilized to provide a uniform and predictable calibration end stop for any of the calibration processes described above, e.g., yaw, pitch, and jaw angle, for smaller instruments. Calibration attachment 2300 is described in greater detail below.

Figure 15:
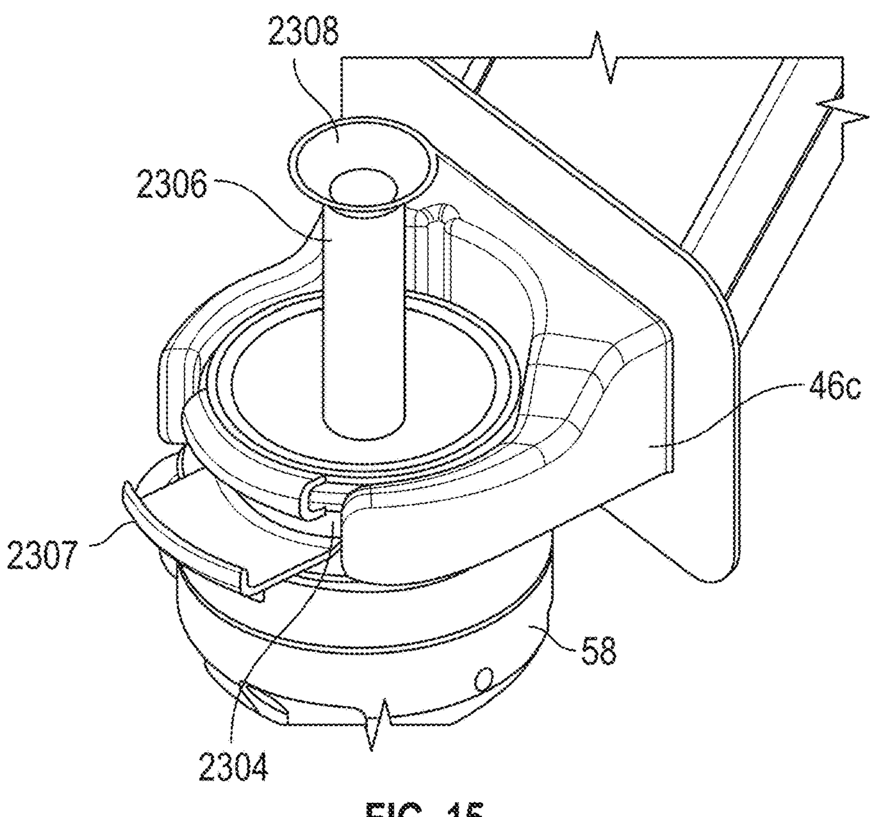
FIG. 15 is an enlarged, perspective view of the calibration attachment of FIG. 14.
Figure 16:
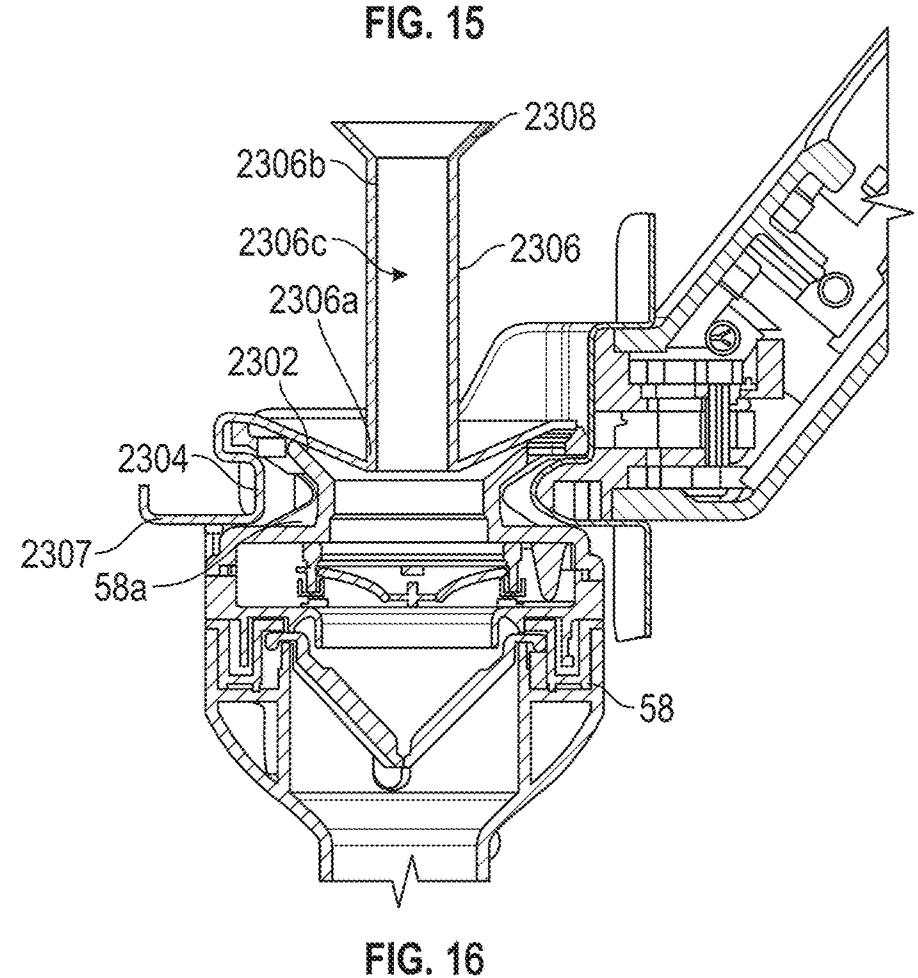
FIG. 16 is a side, cross-sectional view of the calibration attachment of FIG. 14.

Turning to FIGS. 14-16, calibration attachment 2300 includes a base 2302 configured to engage seal housing 58 of cannula 57 using, for example, a clip 2304. Base 2302 may have a circular, concave shape to fit into seal housing 58 to provide for structural rigidity between calibration attachment 2300 and access port 55.

Base 2302 interfaces with seal housing 58 to prevent calibration attachment 2300 from sliding along elongated shaft 2164 of instrument 50 if instrument 50 is being used upside down, i.e., where robotic arm 40 (FIGS. 2 and 3) is rotated such that end effector assembly 2200 is pointing upward. In addition, base 2302 may also strengthen seal housing 58, which may be prone to breakage in response to strain during movement of instrument 50.

Base 2302 is also configured to fit within port latch **46*c*, such that clip 2304 extends between the arms of port latch 46*c* and attaches to a lip 58*a* of seal housing 58. Clip 2304 may also include an extension 2307 which allows for moving clip 2304 in and out of engagement with lip 58*a***.

Calibration attachment 2300 may be formed from any suitable resilient material, such as metals or polymers to allow for flexing of clip 2304. The choice of materials allows for calibration attachment 2300 to be reusable, e.g., autoclavable, or disposable.

Calibration attachment 2300 also includes a tube 2306 extending from base 2302. Tube 2306 includes a first end **2306*a* coupled to base 2302 and a second end 2306*b*. Tube 2306 defines a lumen 2306*c* for passage of instrument 50 therethrough. Tube 2306 may include a funnel 2308 disposed at second open end 2306*b* to aid in insertion of instrument 50 into tube 306. Tube 22306 is centrally aligned with cannula 57 allowing for insertion of instrument 50 into tube 2306 and subsequently into cannula 57. Tube 2306 has a first diameter that is suitable for calibration of end effector assembly 2200. In particular, the first diameter is used as a parameter during the calibration process since it provides a known value to the end stop. The first diameter of tube 2306 may be different from a second diameter of cannula 57. In aspects, a plurality of calibration attachments 2300 may be provided with one of the calibration attachments 2300** being selected for calibration depending upon, for example, the surgical instrument to be calibrated and/or other factors.

Figure 17:
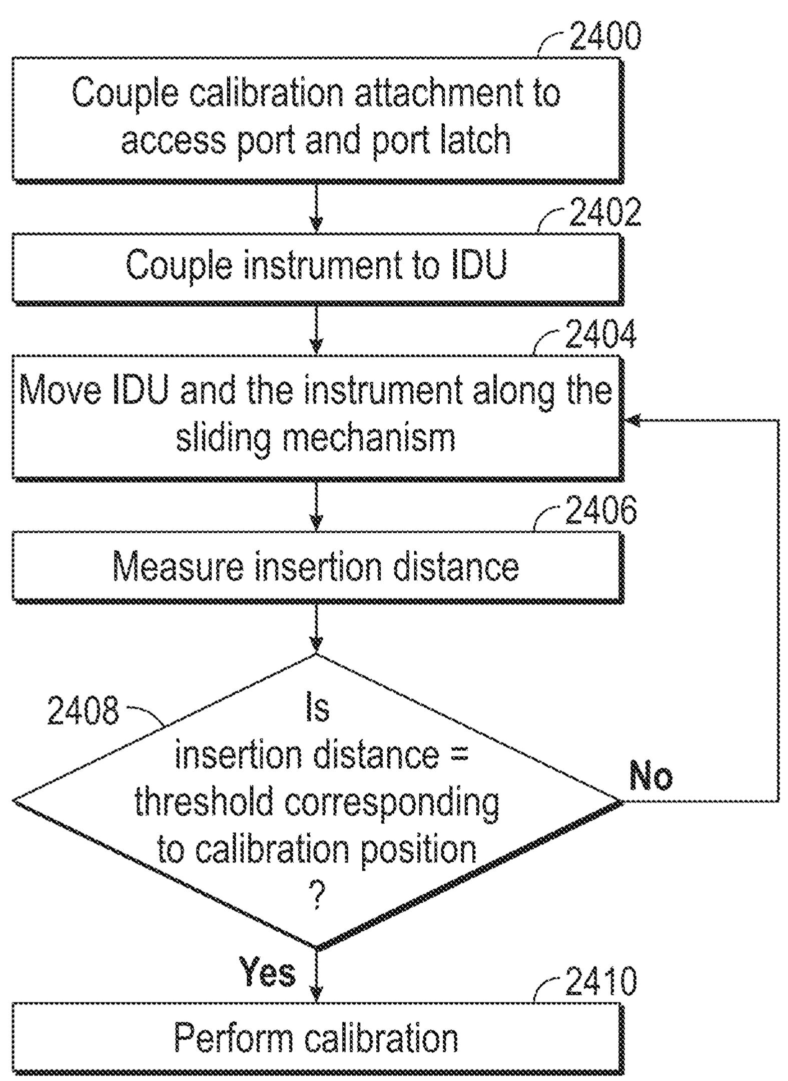
FIG. 17 is a flow diagram illustrating a method for calibrating a surgical instrument using the calibration attachment of FIG. 14 or any other suitable attachment in accordance with this disclosure.

With reference to FIG. 17, in conjunction with FIGS. 2-4 and 12-16, a method for performing a calibration of a surgical instrument or portion thereof in accordance with this disclosure is described. Although described with respect to using calibration attachment 2300 to calibrate end effector assembly 2200 of surgical instrument 50 attached to IDU 52 and configured for use with access port 55, this method of calibration is equally applicable for use with other end effector assemblies, surgical instruments, surgical robotic systems, calibration attachments, and/or access ports. Initially, at step 2400, calibration attachment 2300 is attached to access port 55 and/or port latch **46*c*. More specifically, clip 2304 is attached to lip 58*a* of seal housing 58, thereby securing calibration attachment 2300 to access port 55. At step 2402, instrument 50 is coupled to IDU 52, which establishes mechanical and/or electrical connections therebetween allowing for moving end effector assembly 2200 and instrument 50 by IDU 52 as well as along sliding mechanism 46*a***.

At step 2404, IDU 52 may be zeroed to its starting position such that subsequent movement toward access port 55 is tracked. IDU 52 along with instrument 50 is moved along sliding mechanism **46*a* towards calibration attachment 2300. This may be done automatically upon detection by robotic arm 40 that instrument 50 is coupled to IDU 52**, e.g., detecting that an electrical connection is established therebetween.

As IDU 52 and instrument 50 are moved along sliding mechanism **46*a*, the distance traveled is continually measured at step 2406 using any suitable distance sensor or encoder (not shown) disposed in sliding mechanism 46*a*. The measured distance is provided to IDU controller 41*d* or any other suitable controller of surgical robotic system 10 (FIG. 1) to determine at step 2408 whether end effector assembly 22200 has reached a desired position within tube 306 by comparing the measured distance to a threshold distance. If the threshold distance is not reached, IDU 52 and instrument 50 are advanced farther. Once the threshold is reached, at step 2410, IDU controller 41*d* performs the calibration process for each of the movements of end effector assembly 2200, while end effector assembly 2200 is disposed within tube 2306. This may include calibrating yaw, pitch, and jaw angle of end effector assembly 2200** as described above.

Calibration attachment 2300 may be used with an access port 55 that is larger, e.g., having a 10-15 mm diameter, and, thus, configured accommodate larger endoscopic instruments. Calibration attachment 2300 allows for using smaller and larger instruments through the same access port 55 without removing the access port 55 from robotic arm 40 and/or the patient. The instrument exchange process would only include attaching and/or detaching calibration attachment 2300 and performing the calibration of the instrument 50 prior to its use. In aspects, calibration attachment 2300 may be used with access port 55 having the same diameter, e.g., 8 mm, or smaller.

Figures 18, 19, 20:
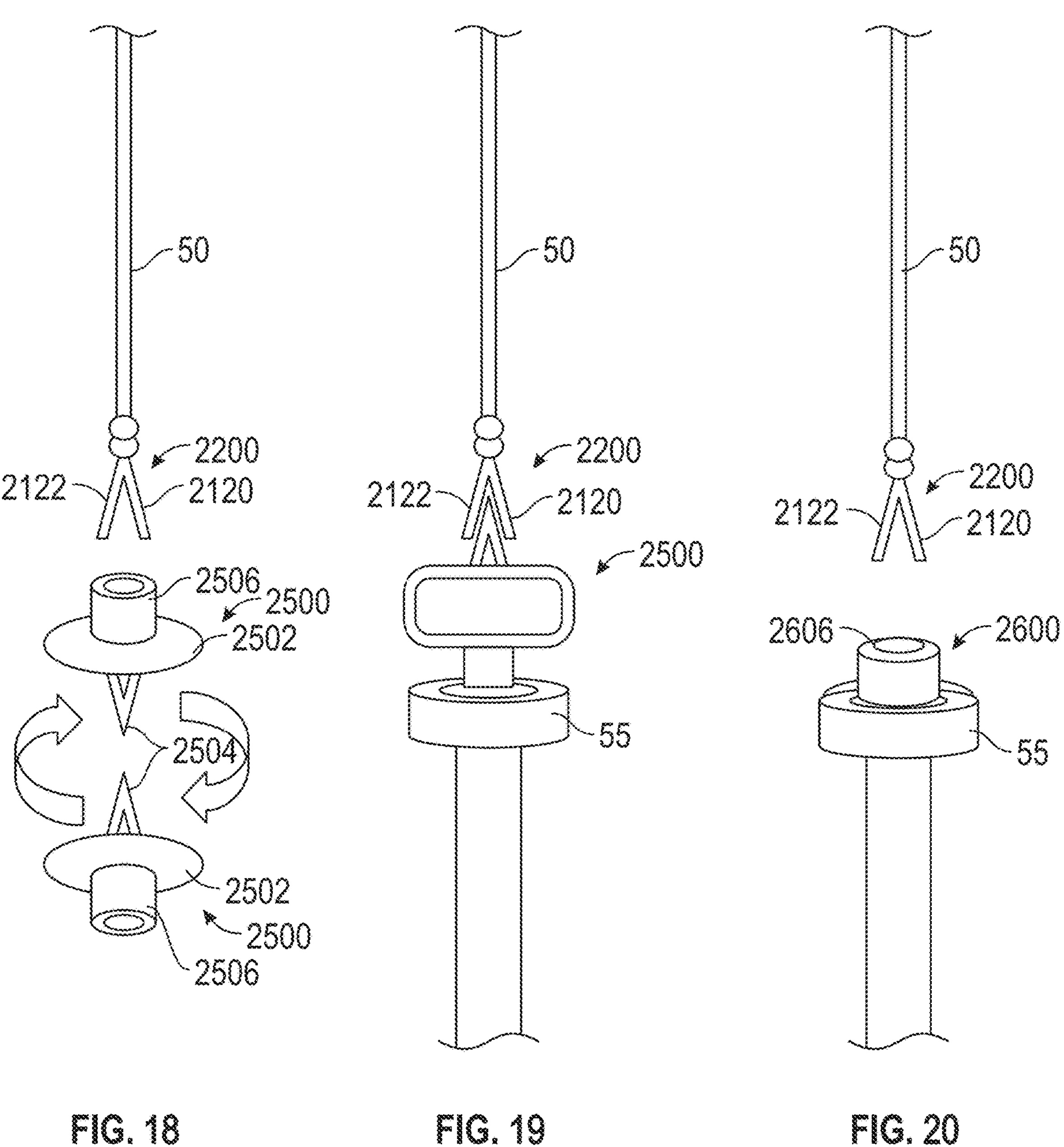
FIG. 18 is a side view of another calibration attachment provided in accordance with this disclosure for calibrating the surgical instrument of FIG. 12 or any other suitable surgical instrument.
FIG. 19 is a side view of the calibration attachment and surgical instrument shown in of FIG. 18.
FIG. 20 is a side view of still another calibration attachment provided in accordance with this disclosure for calibrating the surgical instrument of FIG. 12 or any other suitable surgical instrument.

With reference to FIGS. 18 and 19, another calibration attachment 2500 in accordance with this disclosure is shown including a base 2502 having a wedge 2504 disposed on one side of base 2502 and a tube 2506 disposed on an opposing side of base 2502. Wedge 2504 may have a triangular shape configured to be grasped by jaw members 2120 and 2122 of end effector assembly 2200 of instrument 50 allowing for calibration of the jaw angle. In particular, wedge 2504 has preset dimensions, which may be entered either manually or automatically by reading an RFID tag or another storage medium by robotic arm 40 (FIGS. 2 and 3). During calibration of the jaw angle, jaw members 2120 and 2122 are clamped on wedge 2504 allowing for determining whether the expected or commanded jaw angle matches the preset jaw angle of wedge 2504. Tube 2506 may have any suitable length and may be used in the same manner for calibration as tube 2306 of calibration attachment 2300 (see FIGS. 14-16), as detailed above.

Calibration attachment 2500 may be handheld during use or may be inserted into access port 55 as shown in FIG. 19. Calibration attachment 2500 may be used with one or both of the attachment components, namely, wedge 2504 and/or tube 2506, to calibrate surgical instrument 50. Calibration attachment 2500 is either held with wedge 2504 or tube 2506 toward end effector assembly 2200 and, once that calibration is completed, calibration attachment 2500 is reversed to allow for calibration on the opposing side of calibration attachment 2500 as shown in FIG. 18 with calibration attachment 2500 being rotated in either configuration.

FIG. 20 shows yet another calibration attachment 2600, which is similar to the calibration attachment 2300 (FIGS. 14-16), and also includes a tube 2606, except that tube 2606 is configured to be inserted into access port 55. Tube 2606 is used during calibration of surgical instrument 50 as described above.

While several aspects of this disclosure have been shown in the drawings, it is not intended that this disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. A system, comprising:

a surgical instrument including an articulating shaft and an end effector assembly disposed at a distal end of the articulating shaft, the end effector assembly including:

a clevis defining a longitudinal axis and including first and second arms spaced-apart relative to one another; and first and second jaw members supported by the clevis, at least one of the first or second jaw members movable relative to the other of the first or second jaw members and the clevis between a spaced-apart position and an approximated position for grasping tissue between the first and second jaw members, wherein the clevis includes first and second locating features on outwardly-facing sides of the first and second spaced-apart arms, respectively; and a test fixture, including:

a base including a clevis-receiving area and first and second supports on either side of the clevis-receiving area, the clevis-receiving area configured to receive the clevis of the end effector assembly therein, the first and second supports including first and second retention features, respectively configured to engage the first and second locating features of the clevis, respectively, to thereby engage and align the end effector assembly relative to the test fixture; and at least one sensor configured to obtain a measurement associated with an actuation of the end effector assembly.

2. The system according to claim 1, wherein the first and second locating features define an axis therethrough that is substantially perpendicular relative to the longitudinal axis of the clevis.

3. The system according to claim 1, wherein the first and second locating features are recesses defined within outwardly-facing surfaces of the outwardly-facing sides of the first and second spaced-apart arms, respectively, and wherein the first and second retention features are pins extending inwardly from the first and second supports, respectively.

4. The system according to claim 1, wherein the base of the test fixture further includes a jaw-receiving area configured to receive the first and second jaw members of the end effector assembly therein.

5. The system according to claim 1, wherein the at least one sensor includes at least one of: a jaw pressure or force sensor, a jaw spacing sensor, a knife detection sensor, or an articulation sensor.

6. The system according to claim 1, wherein the at least one sensor includes at least two of: a jaw pressure or force sensor, a jaw spacing sensor, a knife detection sensor, or an articulation sensor.

7. The system according to claim 1, wherein the test fixture includes at least one interchangeable module including the at least one sensor thereon.

8. The system according to claim 1, wherein the at least one of the first or second jaw members is movable between the spaced-apart position and the approximated position with the end effector assembly engaged within the test fixture.

9. The system according to claim 1, wherein the end effector assembly is configured to articulate when engaged within the test fixture to articulate the test fixture therewith.

10. The system according to claim 1, wherein the end effector assembly further includes a knife configured for deployment between the first and second jaw members, the knife deployable with the end effector assembly engaged within the test fixture.

11. The end effector assembly according to claim 1, wherein the sensor is a jaw force sensor that includes a load cell positioned between jaw members.

12. The end effector assembly according to claim 1, wherein the sensor is a thermal camera or a thermal sensor.

13. A system, comprising:

a surgical instrument including an articulating shaft and an end effector assembly disposed at a distal end of the articulating shaft, the end effector assembly including:

a clevis defining a longitudinal axis and including first and second arms spaced-apart relative to one another; and first and second jaw members supported by the clevis, at least one of the first or second jaw members movable relative to the other of the first or second jaw members and the clevis between a spaced-apart position and an approximated position for grasping tissue between the first and second jaw members, wherein the clevis includes first and second locating features on outwardly-facing sides of the first and second spaced-apart arms, respectively; and a test fixture, including a base having a clevis-receiving area and first and second supports on either side of the clevis-receiving area, the clevis-receiving area configured to receive the clevis of the end effector assembly therein, the first and second supports including first and second retention features, respectively configured to engage the first and second locating features of the clevis, respectively, to thereby engage and align the end effector assembly relative to the test fixture.

14. The end effector assembly according to claim 13, wherein the first and second locating features define an axis therethrough that is substantially perpendicular relative to the longitudinal axis of the clevis.

15. The end effector assembly according to claim 13, wherein the second jaw member is fixed relative to the clevis and wherein the first jaw member is pivotable relative to the second jaw member and the clevis.

16. The end effector assembly according to claim 13, wherein the first and second retention features are pins and the first and second locating features are cylindrical holes.

* * * * *